(12) United States Patent
Tousimis et al.

(10) Patent No.: US 6,857,200 B1
(45) Date of Patent: Feb. 22, 2005

(54) SUPERCRITICAL POINT DRYING APPARATUS FOR SEMICONDUCTOR DEVICE MANUFACTURING AND BIO-MEDICAL SAMPLE PROCESSING

(75) Inventors: Anastasios Tousimis, Rockville, MD (US); Chris Tousimis, Cabin John, MD (US)

(73) Assignee: Tousimis Research Corporation, Rockville, MD (US)

(*) Notice: Subject to any disclaimer, the term of this patent is extended or adjusted under 35 U.S.C. 154(b) by 0 days.

(21) Appl. No.: 10/205,394

(22) Filed: Jul. 26, 2002

Related U.S. Application Data

(63) Continuation-in-part of application No. 09/658,185, filed on Sep. 8, 2000, now Pat. No. 6,493,964.
(60) Provisional application No. 60/206,726, filed on May 25, 2000.

(51) Int. Cl.[7] .................................................. F26B 19/00
(52) U.S. Cl. ............................... 34/201; 34/66; 34/236; 34/232
(58) Field of Search .......................... 34/201, 527, 528, 34/292, 233, 237, 337, 236, 342, 351, 470, 66; 134/56 R, 57 R, 94.1, 95.1, 98.1, 902

(56) References Cited

U.S. PATENT DOCUMENTS

| | | | |
|---|---|---|---|
| 3,886,047 A | | 5/1975 | Billups, Jr. |
| 4,003,135 A | | 1/1977 | Baker et al. |
| 4,055,904 A | * | 11/1977 | Horne ........................... 34/530 |
| 4,104,808 A | | 8/1978 | Horne et al. |
| 5,267,455 A | | 12/1993 | Dewees et al. |
| 5,937,675 A | * | 8/1999 | Stucker ........................ 68/18 R |
| 6,067,728 A | * | 5/2000 | Farmer et al. ................. 34/470 |
| 6,294,194 B1 | | 9/2001 | Horhota et al. |
| 6,306,564 B1 | * | 10/2001 | Mullee ........................ 430/329 |
| 6,306,654 B1 | | 10/2001 | Boime et al. |

* cited by examiner

Primary Examiner—Henry Bennett
Assistant Examiner—Camtu Nguyen
(74) Attorney, Agent, or Firm—Sughrue Mion, PLLC

(57) ABSTRACT

A critical point drying apparatus for sample preparation in electron microscopy and semiconductor wafer production includes a computer system to automate the operational modes in drying the specimen. These operational modes controlled by the computer system are: cooling, in which a drying chamber is cooled; starting, in which the specimen chamber is filled with a transitional fluid; purging, in which the transitional fluid purges an intermediary fluid from the drying chamber and the purged internediary fluid is collected by a collector condenser; heating, in which the drying chamber is heated to elevate the transitional fluid to its critical point temperature and pressure; and bleeding, in which the drying chamber is depressurized to atmospheric pressure at a very slow rate until the drying chamber is completely vented, which signals the end of the drying operation. The drying chamber incorporates concave surfaces for pressure dispersal and to facilitate purging the intermediary fluid completely. The drying chamber incorporates angled inlet ports and windows that are sealed with gaskets. The drying chamber also incorporates the usage of a wafer holder, spacer rings and inserts to allow for the secure suspension of wafers being processed. Passing the cooling fluid through a closed loop refrigeration system may also cool the drying chamber.

30 Claims, 20 Drawing Sheets

INTO WAFER HOLDER

INTO CHAMBER

| MODE | COOL VALVE | FILL VALVE | PURGE VALVE | BLEED VALVE | VALVE OPERATIONS |
|---|---|---|---|---|---|
| COOL | OPEN | CLOSED | CLOSED | CLOSED | COOL VALVE STAYS OPEN UNTIL CHAMBER TEMPERATURE < 5° C |
| FILL (1) | AS NEEDED | OPEN | CLOSED | CLOSED | PRESET BASED ON CHAMBER SIZE; COOL VALVE CYCLES TO KEEP CHAMBER TEMPERATURE < 5° C |
| PURGE | AS NEEDED | OPEN | OPEN | CLOSED | PRESET BY OPERATOR; COOL VALVE CYCLES TO KEEP CHAMBER TEMPERATURE < 5° C |
| FILL (2) | AS NEEDED | OPEN | CLOSED | CLOSED | PRESET BASED ON CHAMBER SIZE; COOL VALVE CYCLES TO KEEP CHAMBER TEMPERATURE < 5° C |
| HEAT | CLOSED | CLOSED | CLOSED | CLOSED | |
| BLEED | CLOSED | CLOSED | CLOSED | OPEN | BLEED VALVE CLOSES WHEN PRESSURE < 400 PSI |
| VENT | CLOSED | CLOSED | OPEN | CLOSED | PURGE VALVE STAYS OPEN UNTIL POWER IS TURNED OFF |

*FIG. 16*

SUPERCRITICAL POINT DRYING APPARATUS FOR SEMICONDUCTOR DEVICE MANUFACTURING AND BIO-MEDICAL SAMPLE PROCESSING

CROSS-REFERENCES TO RELATED APPLICATIONS

1. This is a continuation-in-part of Application Ser. No. 09/658,185 filed Sep. 8, 2000, now U.S. Pat. No. 6,493,964 the disclosure of which is incorporated herein by reference. application Ser. No. 09/658,185 was filed under 35 U.S.C. § 111(a) claiming benefit pursuant to 35 U.S.C. § 119(e)(1) of the filing dates of Provisional Application No. 60/206,726 filed on May 25, 2000 pursuant to 35 U.S.C. § 111(b).

BACKGROUND OF THE PRESENT INVENTION

1. Technical Field of the Present Invention

This present invention relates to improvements in critical point dryers for sample preparation for electron microscopy and semiconductor wafer manufacturing and especially to a computer controlled critical point drying apparatus. The present invention is embodied in a method for controlling a critical point drying apparatus using a computer system, a computer system for implementing the method of controlling the critical point drying apparatus, and a computer program product bearing software instructions that implement the method of controlling the critical point drying apparatus.

2. Description of the Related Art

The following references provide useful background information on the indicated topics, all of which relate to the present invention, and are incorporated herein by reference:

U.S. Pat. No. 4,055,904 issued to Home on Nov. 1, 1977 describes an automatic method of operating the purge and bleed modes for a critical point dryer.

U.S. Pat. No. 4,104,808 issued to Home et al. on Aug. 8, 1978 describes a critical point dryer wherein the purge and bleed modes are controlled semi automatically.

There will now be provided a discussion of various topics to provide a proper foundation for understanding the present invention.

In order to examine biological specimens under a scanning electron microscope, the biological specimens must be completely dried and coated with a thin conductive layer. It is important that the drying process be accomplished without disturbing the microstructure of the biological specimen to be examined. Depending upon the biological specimen's structure, three techniques are available for drying the biological specimen. The first method is air drying by evaporation of the cellular water. While suitable for bacteria or other rigid structures, this method is detrimental to the structures of many biological specimens. The surface tension forces, which turn a grape into a raisin during the drying process, cause sufficient distortion in the cell structure of many biological specimens thereby rendering them useless. The second method is sublimation or freeze-drying. This method is useful only for very small specimens. Additionally, unless the lengthy technique is followed precisely, structural damage from thermal expansion or ice crystal formation often results. The third method utilized is the phase transitional or critical point drying which produces consistently reproducible results without the drawbacks of the preceding two methods.

Along with being used to prepare specimens for the scanning electron microscope, critical point drying may also be used in the production of MEMS (Micro-Electro-Mechanical Systems) devices. The critical point drying process helps for a sticktion free release of microstructers in the MEMS device.

In critical point drying, a dehydrating fluid such as ethanol or acetone gradually replaces the water contained in a specimen. This maintains the three-dimensional hydrated morphology of the structure under study. However, if the ethanol or acetone evaporates, surface tension forces would cause structural damage and destroy the specimen's usefulness.

Critical point drying devices for sample preparation in electron microscopy are known in the art. The prior art critical point dryers utilize the technique of substituting a transitional fluid for the dehydrating fluid in the cell structure and then removing the transitional fluid. A critical point dryer heats and pressurizes the biological specimen until above the critical pressure and critical temperature. The critical temperature is defined as the temperature above which a gas cannot be liquefied by pressure alone. The critical pressure is the pressure that results when a substance exists as a gas and a liquid in equilibrium at the critical temperature. The critical point of a liquid is when its temperature and pressure are at or above the critical temperature and pressure and the densities of the liquid phase and vapor phase are identical. This critical point is characterized by an absence of phase boundaries that normally exist between a liquid and its vapor at temperatures and pressures below the critical point. This absence of a phase boundary eliminates the boundary forces that exist when changing a liquid to a gas. These boundary forces often cause the destruction of the extremely delicate specimens when changing its internal liquid to a gas below the critical point. Therefore, the solution which is applied in a critical point drying process is to remove the internal liquid from the biological specimen above its critical pressure and temperature to eliminate the boundary force destruction that would otherwise result.

Although all fluids have a characteristic critical point which should allow direct removal without the use of dehydrating or transitional fluids, the critical point temperature and pressure of water is 374.2° C. and 218 atmospheres. Achieving these temperatures and pressures would cause severe damage to most biological specimens and therefore a fluid having a lower critical temperature and pressure is normally substituted. Commonly, a dehydrating fluid is used that is miscible with water (e.g., ethanol or acetone) as an intermediate stage between the specimen containing water and a specimen containing transitional fluid.

Typically, and in the prior art dryers, the transitional fluid commonly used is carbon dioxide ($CO_2$) because it is easy to use, more economical, less noxious and provides consistently better results than other transitional fluids. The critical temperature and pressure of carbon dioxide is 31° C. and 1,072 psi, respectively, thus reducing the potential for destruction of the specimen structure.

The known instruments and apparatuses for critical point drying of biological specimens include, of course, a drying chamber that is connected a supply of the transitional fluid with various regulating valves, temperature gauges and a means for heating the chamber. A skilled technician must carefully control the application, heating, pressurizing and removal of the transitional fluid, thus requiring not only time but also constant attention. Applicants are unaware of a computer-controlled critical point drying apparatus that eliminates the need for constant operator attention.

SUMMARY OF THE PRESENT INVENTION

The present invention has been made in view of the above circumstances and to overcome the above problems and limitations of the prior art.

Additional advantages of the present invention will be set forth in part in the description that follows and in part will be obvious from the description, or may be learned by practice of the present invention. The advantages of the present invention may be realized and attained by means of the instrumentalities and combinations particularly pointed out in the appended claims.

According to a first aspect of the invention, a critical point drying chamber for drying specimens comprising a chamber and at least one heater is provided. The apparatus further comprises a first valve assembly that supplies a cooling fluid to the chamber. The apparatus further comprises a second valve assembly that supplies a transitional fluid having a critical point temperature and critical point pressure to the chamber. The apparatus further comprises a third valve assembly that allows an intermediary fluid to be purged from the chamber. The apparatus further comprises a fourth valve assembly that bleeds the transitional fluid from the chamber. The apparatus further comprises a condenser collector that collects intermediary fluid exiting the third valve assembly.

According to a second aspect of the invention, a critical point drying apparatus for drying specimens comprises a cylindrical drying chamber having concave end portions and at least one heater. The apparatus further comprises a first valve assembly that supplies a cooling fluid to the drying chamber. The apparatus further comprises a second valve assembly that supplies a transitional fluid having a critical point temperature and critical point pressure to the drying chamber. The apparatus further comprises a third valve assembly that allows an intermediary fluid to be purged from the drying chamber. The apparatus further comprises a fourth valve assembly that bleeds the transitional fluid from the drying chamber.

According to a third aspect of the invention, a critical point drying apparatus for drying specimens comprises a drying chamber having at least one heater. The apparatus further comprises a first valve assembly that supplies a cooling fluid to the drying chamber. The apparatus further comprises a second valve assembly that supplies a transitional fluid having a critical point temperature and critical point pressure to the drying chamber. The apparatus further comprises a third valve assembly that allows an intermediary fluid to be purged from the drying chamber. The apparatus further comprises a fourth valve assembly that bleeds the transitional fluid from the drying chamber. The apparatus further comprises a computer system that operates the first, second, third and fourth valve assemblies and that activates the at least one heater to heat the transitional fluid above the critical point temperature and to pressurize the transitional fluid above the critical point pressure.

According to a fourth aspect of the invention, a critical point drying apparatus for drying specimens, comprising a drying chamber having concave end portions and at least one heater is provided. The apparatus further comprises a first valve assembly that supplies a cooling fluid to the drying chamber wall. The apparatus further comprises a second valve assembly that supplies a transitional fluid having a critical point temperature and critical point pressure to the interior of the drying chamber. The apparatus further comprises a third valve assembly that allows an intermediary fluid to be purged from the interior of the drying chamber. The apparatus further comprises a fourth valve assembly that bleeds the transitional fluid from the interior of the drying chamber at a predetermined rate. The apparatus further comprises a computer system that operates the first, second, third and fourth valve assemblies and that activates the at least one heater to heat the transitional fluid above the critical point temperature and to pressurize the transitional fluid above the critical point pressure.

According to a fifth aspect of the invention, a critical point dryer apparatus comprising a drying chamber and a computer system wherein the computer system is adapted to controlling the drying chamber during a critical point drying process is provided. The computer system comprises a processor and a memory comprising software instructions adapted to enable the computer system. The software instructions enable the computer system to cool the drying chamber to a first chamber temperature. The software instructions further enable the computer system to fill the drying chamber with a transitional fluid having a critical point temperature and critical point pressure while maintaining the drying chamber at the first chamber temperature such that the transitional fluid completely displaces an intermediary fluid within a first time period. The software instructions further enable the computer system to activate at least one heater to raise the transitional fluid to its critical point pressure and critical point temperature, thereby reaching critical point equilibrium. The software instructions farther enable the computer system to maintain the transitional fluid at the critical point equilibrium for a second time period. The software instructions further enable the computer system to bleeding the transitional fluid from the drying chamber while maintaining the drying chamber at the second chamber temperature and allowing the drying chamber pressure to drop.

According to a sixth aspect of the invention, a computer program product for enabling a computer system to control the drying chamber during a critical point drying process is provided. The computer program product comprises software instructions for enabling the computer system to perform predetermined operations, and a computer readable medium bearing the software instructions. The predetermined operations comprise cooling the drying chamber to a first chamber temperature. The predetermined operations comprise filling the drying chamber with a transitional fluid having a critical point temperature and critical point pressure while maintaining the drying chamber at the first chamber temperature such that the transitional fluid completely displaces the intermediary fluid within a first time period. The predetermined operations comprise activating at least one heater to raise the transitional fluid to its critical point pressure and critical point temperature, thereby reaching critical point equilibrium. The predetermined operations comprise maintaining the transitional fluid at the critical point equilibrium for a second time period. The predetermined operations comprise bleeding the transitional fluid from the drying chamber while maintaining the drying chamber at the second chamber temperature.

According to a seventh aspect of the invention, an article of manufacture, which comprises a computer readable medium having stored therein a computer program to control a drying chamber during a critical point drying process, is provided. The article of manufacture comprises a first code segment which, when executed on a computer, cools the drying chamber to a first chamber temperature. The article of manufacture comprises a second code segment which, when executed on a computer, fills the drying chamber with a transitional fluid having a critical point temperature and critical point pressure while maintaining the drying chamber at the first chamber temperature such that the transitional fluid completely displaces the intermediary fluid within a first time period. The article of manufacture comprises a third code segment which, when executed on a computer, activates at least one heater to raise the transitional fluid to its critical point pressure and critical point temperature, thereby reaching a critical point equilibrium. The article of manufacture comprises a fourth code segment which, when executed on a computer, maintains the transitional fluid at the critical point equilibrium for a second time period. The article of manufacture comprises a fifth code segment which, when executed on a computer, bleeds the transitional fluid from the drying chamber while maintaining the drying chamber at the second chamber temperature.

According to an eighth aspect of the invention, a critical point drying chamber for drying specimens, comprising a chamber with a heater is provided. The critical point drying apparatus further comprises a first valve assembly that supplies a cooling fluid to the chamber, and a second valve assembly that supplies a transitional fluid having a critical point temperature and critical point pressure to the chamber. The critical point drying chamber further comprises a third valve assembly that allows an intermediary fluid to be purged from the chamber, and that bleeds the transitional fluid from the chamber, and a condenser collector that collects intermediary fluid exiting the third valve assembly. The drying chamber further comprises a wafer holder, and a chamber insert to change the inner diameter of the drying chamber.

According to a ninth aspect of the invention, a critical point drying chamber for drying specimens, comprising a chamber with a heater is provided. The drying chamber is a cylindrical drying chamber having concave end portions and a first valve assembly that supplies a cooling fluid to the drying chamber. The critical point drying apparatus further comprises a second valve assembly that supplies a transitional fluid having a critical point temperature and critical point pressure to the drying chamber, and a third valve assembly that allows an intermediary fluid to be purged from the drying chamber; and that bleeds the transitional fluid from the drying chamber. The drying chamber further comprises a wafer holder, and a chamber insert to change the inner diameter of the drying chamber.

According to a tenth aspect of the invention, a critical point drying chamber for drying specimens, comprising a chamber with a heater is provided. The critical point drying chamber further comprises a first valve assembly that supplies a cooling fluid to the drying chamber, a second valve assembly that supplies a transitional fluid having a critical point temperature and critical point pressure to the drying chamber, and a third valve assembly that allows an intermediary fluid to be purged from the drying chamber, and that bleeds the transitional fluid from the drying chamber. The critical point drying apparatus further comprises a computer system that operates the first, second and third valve assemblies and that activates the heater to heat the transitional fluid above the critical point temperature and to pressurize the transitional fluid above the critical point pressure. The drying chamber further comprises a wafer holder, and a chamber insert to change the inner diameter of the drying chamber.

According to an eleventh aspect of the invention, a critical point drying chamber for drying specimens, comprising a chamber with a heater is provided. The drying chamber is a cylindrical drying chamber having concave end portions and a first valve assembly that supplies a cooling fluid to the drying chamber. The critical point drying apparatus further comprises a second valve assembly that supplies a transitional fluid having a critical point temperature and critical point pressure to the drying chamber, and a third valve assembly that allows an intermediary fluid to be purged from the drying chamber, and that bleeds the transitional fluid from the drying chamber. In addition, the critical point drying apparatus furtherer comprises a computer system that operates the first, second and third valve assemblies and that activates the heater to heat the transitional fluid above the critical point temperature and to pressurize the transitional fluid above the critical point pressure. The drying chamber further comprises a wafer holder, and a chamber insert to change the inner diameter of the drying chamber.

The above advantages of the present invention will become apparent from the following detailed description and with reference to the accompanying drawing figures.

BRIEF DESCRIPTION OF THE DRAWINGS

The accompanying drawings, which are incorporated in and constitute a part of this specification illustrate embodiments of the present invention and, together with the written description, serve to explain the advantages and principles of the present invention. In the drawings.

FIG. 16 is a table showing the valve openings and closings for each drying mode controlled by the computer system.

DESCRIPTION OF THE PREFERRED EMBODIMENTS

Figure 1:
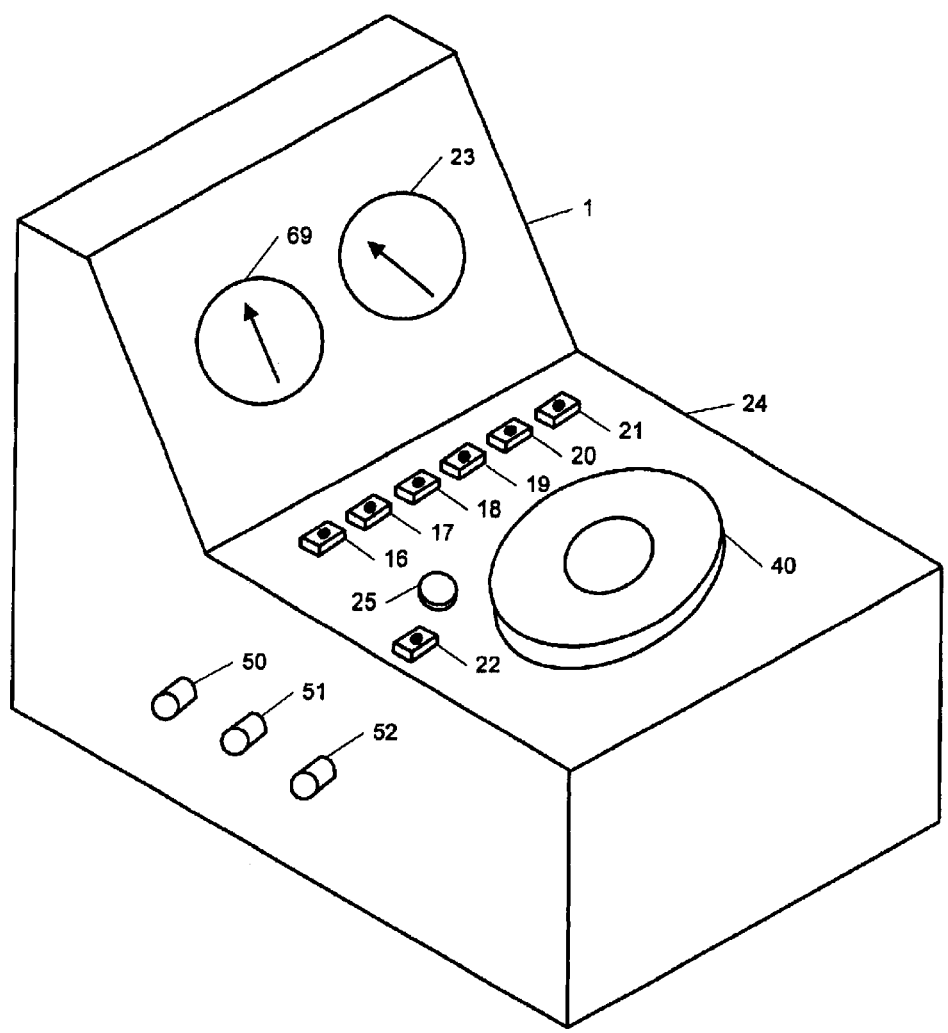
FIG. 1 illustrates a perspective view of a first embodiment of the invention.

1. Prior to describing the aspects of the present invention, some details concerning certain terms of art will be provided to facilitate the reader's understanding of the present invention and to set forth the meaning of various terms.

As used herein, the term "computer system" encompasses the widest possible meaning and includes, but is not limited to, microprocessors, standalone processors, networked processors, mainframe processors, and processors in a client/server relationship. The term "computer system" is to be understood to include at least a memory and a processor. In general, the memory will store, at one time or another, at least portions of executable program code, and the processor will execute one or more of the instructions included in that executable program code.

As used herein, the term "embedded computer system" includes, but is not limited to, an embedded central processor and memory bearing object code instructions. Examples of embedded computer systems include, but are not limited to, personal digital assistants, cellular phones and digital cameras. In general, any device or appliance that uses a central processor, no matter how primitive, to control its functions can be labeled has having an embedded computer system. The embedded central processor will execute one or more of the object code instructions that are stored on the memory. The embedded computer system can include cache memory, input/output devices and other peripherals.

It will be appreciated that the term "predetermined operations" and the term "computer system software" mean substantially the same thing for the purposes of this description. It is not necessary to the practice of this present invention that the memory and the processor be physically located in the same place. That is to say, it is foreseen that the processor and the memory might be in different physical pieces of equipment or even in geographically distinct locations.

As used herein, one of skill in the art will appreciate that "media" or "computer-readable media" may include a diskette, a tape, a compact disc, an integrated circuit, a cartridge, a remote transmission via a communications circuit, or any other similar medium useable by computers. For example, to distribute computer system software, the supplier might provide a diskette or might transmit the instructions for performing predetermined operations in some form via satellite transmission, via a direct telephone link, or via the Internet.

Although computer system software might be "written on" a diskette, "stored in" an integrated circuit, or "carried over" a communications circuit, it will be appreciated that, for the purposes of this discussion, the computer usable medium will be referred to as "bearing" the instructions for performing predetermined operations. Thus, the term "bearing" is intended to encompass the above and all equivalent ways in which instructions for performing predetermined operations are associated with a computer usable medium.

Therefore, for the sake of simplicity, the term "program product" is hereafter used to refer to a computer useable medium, as defined above, which bears instructions for performing predetermined operations in any form.

A detailed description of the preferred embodiments of the present invention will now be given referring to the accompanying drawings wherein like reference numerals refer to similar parts in the several views.

The general operation of a critical point dryer will be provided to facilitate the reader's understanding of the present invention. This description of the general operation of a critical point dryer is by no means limiting on the operation of the present invention. The first step in a critical point drying operation is to cool the drying chamber to a temperature that will condense the transitional fluid to be added later. A cooling fluid flows around the drying chamber and evaporates in a heat exchange relationship with the drying chamber. Preferably, the cooling fluid is liquid carbon dioxide. If a closed loop refrigeration system is used to cool the drying chamber, Freon™ or its equivalent can also be used. Next, the treated specimen is placed in the drying chamber along with an amount of the dehydrating fluid, such as ethanol, methanol or acetone. The specimen has previously been dehydrated with the dehydrating fluid. After the treated specimen has been placed in the drying chamber and the cover secured, a transitional fluid fills the drying chamber. After the drying chamber is filled, the dehydrating fluid is purged from the treated specimen in the drying chamber. Preferably, the transitional fluid is liquid carbon dioxide. The purging of the dehydrating fluid is controlled over a predetermined time period. In an aspect of the invention, the critical point drying apparatus cycles through another filling of the drying chamber with the transitional fluid to ensure that the transitional fluid completely fills the drying chamber. The drying chamber is then heated to raise the transitional fluid to its critical point pressure and critical point temperature, thereby reaching critical point equilibrium. Once critical point equilibrium is reached, the equilibrium is maintained for a certain length of time. After the equilibrium time period has expired, the drying chamber temperature is maintained while the drying chamber pressure is reduced or bled-off very slowly. When the drying chamber pressure drops below a predetermined threshold, the drying chamber is then vented to release any residual pressure that may hinder removal of the chamber cover and the chamber heat is shut off.

Referring to FIG. 1, a perspective view showing the external configuration of an embodiment of the critical point drying apparatus 1 is shown. The housing 24 encloses the internal valves, wiring, piping, switches, relays and computer system components that make up the critical point drying apparatus 1. A power switch 22 applies electrical power to the dryer through a fuse. The operation indicator lights indicate the individual operation that is being undertaken in the drying chamber 40. Preferably, the operation indicators are light emitting diodes (LED). The critical point drying apparatus 1 has the following operation indicators: cool LED 16, fill LED 17, purge LED 18, heat LED 19, bleed LED 20 and vent LED 21. The temperature gauge 23 and the pressure gauge 69 provide visible indicators of the present conditions within the drying chamber 40. Transitional fluid and cooling fluid enter the critical point drying apparatus 1 through the inlet port 52. Exhausted cooling fluid exits the critical point drying apparatus 1 through the cool exit port 51. Purged dehydrating fluid and exhausted transitional fluid exits the critical point drying apparatus 1 through purge port 50.

Figure 2:
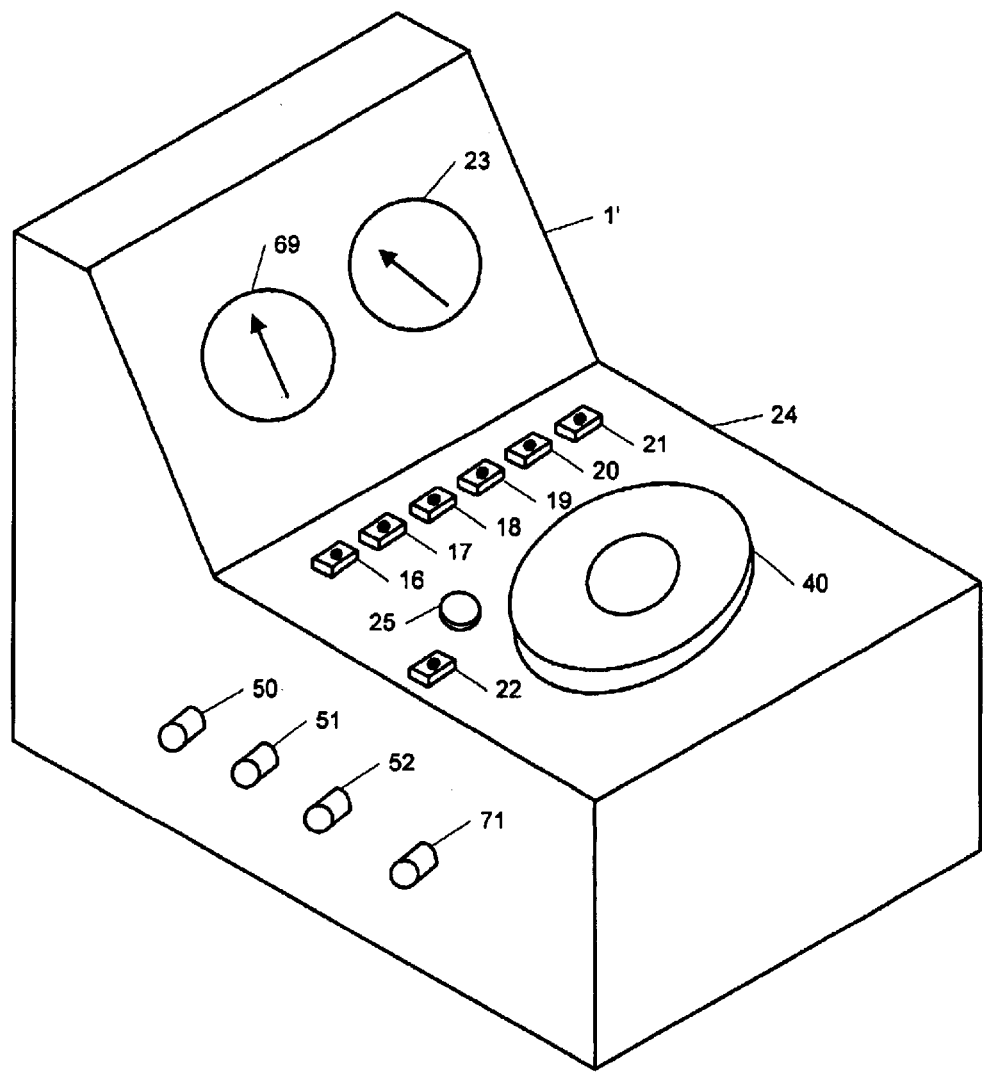
FIG. 2 illustrates a perspective view of a second embodiment of the invention.

Referring to FIG. 2, a perspective view showing the external configuration of another embodiment of the critical point drying apparatus 1' is shown. The critical point drying apparatus 1' is shown with a cool supply port 71. The cool supply port 71 is connected to a closed loop refrigeration system. Cooling fluid circulates through the critical point drying apparatus 1' by entering the cool supply port 71 and exiting through the cool exit port 51. Transitional fluid enters the critical point drying apparatus 1' through the inlet port 52. Purged dehydrating fluid and exhausted transitional fluid exits the critical point drying apparatus 1' through purge port 50.

Figure 3:
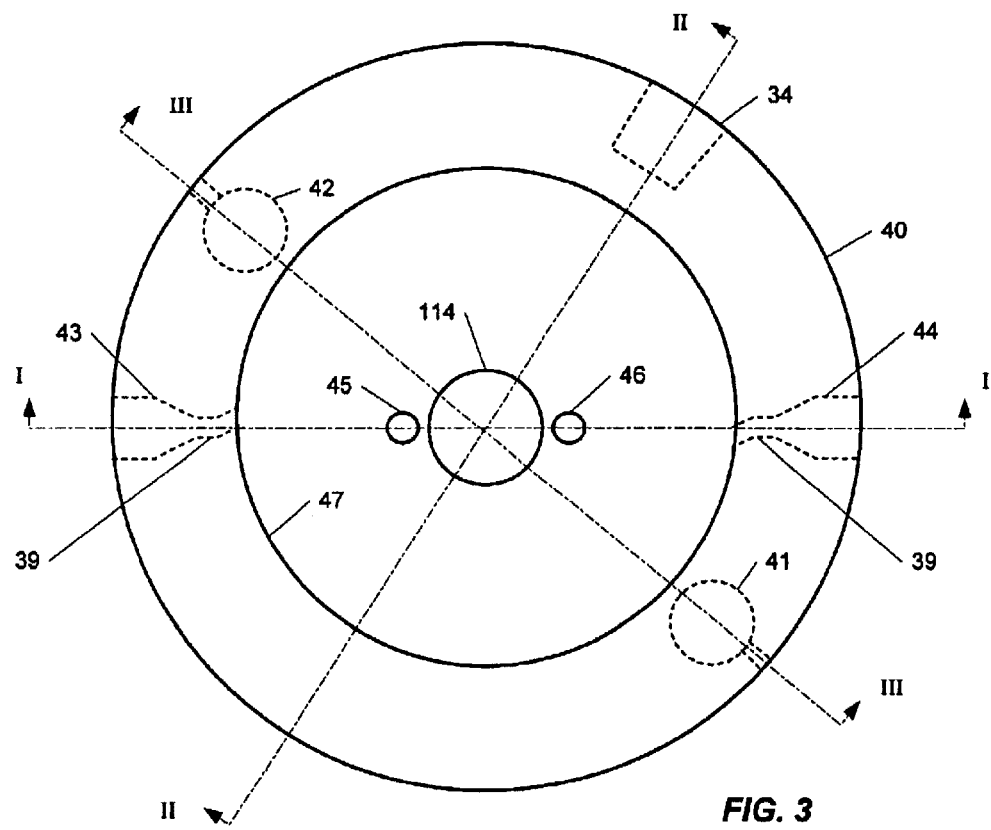
FIG. 3 is a top view of the drying chamber illustrating the location of the purge outlets, the fill inlets, the cool inlet and the cool outlet.

Referring to FIG. 3, a top view of the drying chamber 40 is illustrated. The placement of the various inlets and outlets shown in FIG. 3 is by no means limiting and is shown for illustration purposes only. The cross-sectional view along lines I—I includes the fill inlets and the purge ports and is shown in more detail in FIG. 6. The cross-sectional view along lines II—II includes the heater and is shown in more detail in FIG. 7. The cross-sectional view along lines III—III includes the cool inlet and the cool outlet and is shown in more detail in FIG. 8. As shown in FIG. 3, the fill inlets 43,44 have an angled portion 39 that is angled relative to the drying chamber wall 47 such that when the transitional fluid enters the drying chamber 40, it will flow into the drying chamber 40 in a swirling fashion. The swirling of the transitional fluid as it enters the drying chamber 40 allows for an even and thorough purge of the intermediary fluid from the drying chamber 40.

Figure 4:
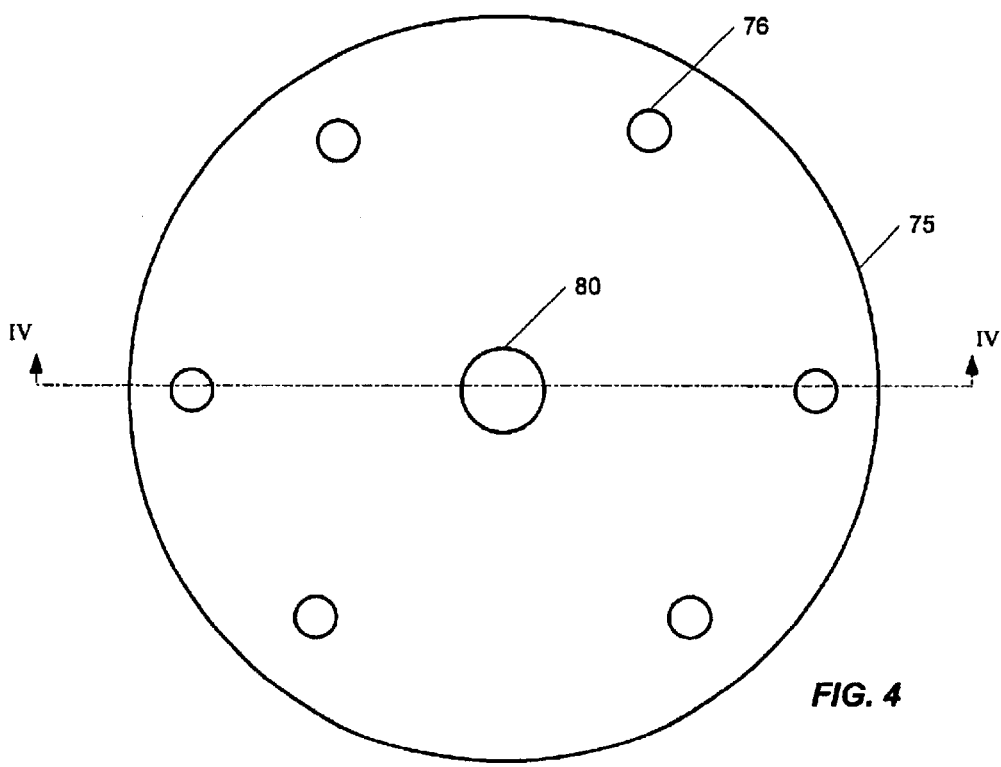
FIG. 4 is a top view of the chamber cover.

Referring to FIG. 4, a top view of the chamber cover 75 is illustrated. Cross-section IV—IV includes the mounting stud holes 76 and is shown in more detail in FIG. 5. The chamber cover 75 has a cover viewing port 80 for observing the interior of the drying chamber 40. Preferably, the mounting stud holes 76 are evenly arranged around the perimeter of the chamber cover 75.

Figure 5:
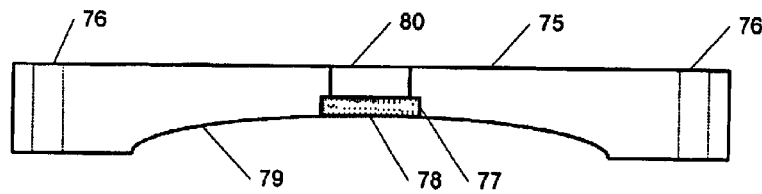
FIG. 5 illustrates a cross-sectional view along lines IV—IV of the chamber cover, the cover viewing port and the cover viewing window.

Referring to FIG. 5, the cross-section of the chamber cover 75 along lines IV—IV is illustrated in more detail. This is the cross-section along lines IV—IV referred to by FIG. 4. The chamber cover 75 secured by securing knobs (not shown) and is provided with a cover viewing window 78 for viewing the specimen during the operation of the critical point drying apparatus 1.

The cover viewing window 78 is mounted on the axial center of the chamber cover 75. Preferably, the cover viewing window 78 comprises quartz or an equivalent material. The operator can view the interior of the drying chamber 40 through the cover viewing port 80 in the chamber cover 75 and monitor the progress of the critical point drying sequence. The cover viewing window 78 is mounted with a precision machined viewing window gasket 77 that is pressure fit into the cover viewing port 80 in the chamber cover 75. Preferably, the viewing window gasket 77 comprises Teflon™ or an equivalent material. The viewing window gasket 77 holds the cover viewing window 78 in place, thereby providing a seal that withstands high pressure and will not be damaged by the intermediary fluids.

In an aspect of the invention, the chamber cover 75 has a concave surface 79 on its underside that has a concave pitch. The concave pitch acts to evenly displace the internal pressure of the drying chamber 40 exerted on the chamber cover 75. The concave surface 79 allows the critical point drying apparatus 1 to accommodate large specimens without warping the chamber cover 75. For example, wafers used in integrated circuit manufacturing can be upwards of twelve inches in diameter. A conventional chamber cover would likely warp and be difficult to remove from the drying chamber.

Figure 6:
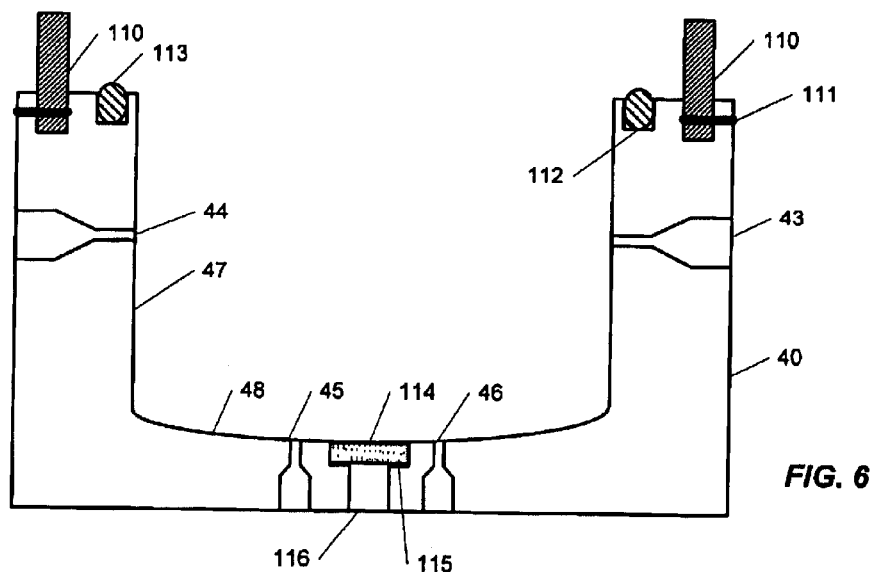
FIG. 6 illustrates a cross-sectional view of the drying chamber along lines I—I showing the fill inlets, the purge outlets, the chamber viewing port and the chamber viewing window.

Referring to FIG. 6, the cross-section of the drying chamber 40 along lines I—I will be described in more detail. The drying chamber 40 is also provided with a fill inlets 43,44 and a purge outlets 45,46 that allow the transitional fluid to fill and flow through the chamber. As the size (i.e. diameter) of the drying chamber 40 increases, the fill inlets 43,44 and the purge outlets 45,46 serve to increase the efficiency of the critical point drying apparatus 1. The fill inlet 43,44 has an angled portion 39 that is angled relative to the drying chamber wall 47 such that when the transitional fluid enters the drying chamber 40, it will flow into the drying chamber 40 in a swirling fashion. The swirling of the transitional fluid as it enters the drying chamber 40 allows for an even and thorough purge of the intermediary fluid from the drying chamber 40. A small chamber may require only a single fill inlet 43 and a single purge outlet 45 to adequately flow the transitional fluid through the drying chamber 40. However, as drying chamber size increases, a plurality of fill inlets 43,44, are used and all have an angled portion 39 that is arranged at an angle relative to the drying chamber wall 47, which efficiently circulates the incoming transitional fluid. An added benefit of multiple fill inlets is that the drying chamber 40 fills at a much faster rate, thereby inducing less disturbance to the specimen situated in the drying chamber 40. Similarly, a large drying chamber has a plurality of purge outlets 45,46 situated at the lowest point of the drying chamber 40 that aids in the collection and purging of the intermediary fluid.

The drying chamber 40 has a chamber viewing window 114 mounted in the axial center of the drying chamber 40. Preferably, the chamber viewing window 114 comprises quartz or an equivalent material. The chamber viewing window 114 is lighted from below and the operator can view the interior of the drying chamber 40 through the cover viewing port 80 in the chamber cover 75 and monitor the progress of the critical point drying sequence. The chamber viewing window 114 is mounted with a precision machined viewing window gasket 115 that is pressure fit into a chamber viewing port 116 in the bottom of the drying chamber 40. Preferably, the viewing window gasket 115 comprises Teflon™ or an equivalent material. The viewing window gasket 115 holds the chamber viewing window 114 in place, thereby providing a seal that withstands high pressure and will not be damaged by the intermediary fluids.

Mounting studs 110 extend upward through the chamber cover 75 and in conjunction with internally threaded securing knobs (not shown), fixably and sealably mount the chamber cover 75 to the drying chamber 40. By drilling through the drying chamber wall 47 into the mounting studs 110, stainless steel mounting pins 111 can be inserted into the mounting studs 110 to prevent any movement.

The bottom of the drying chamber 40 has a chamber concave surface 48 with a concave pitch. The concave pitch acts to each active to evenly displace the internal pressure of the drying chamber 40. The chamber concave surface 48 allows the intermediary fluid to collect and exit through the purge ports 45,46 that are located at the lowest point of the drying chamber. The concavity thus assists with dispersing the internal pressure and with the complete purging of the intermediary fluid through the bottom of the drying chamber 40. The chamber concave surface 48 allows the critical point drying apparatus 1 to accommodate large specimens without warping in the chamber cover 75.

A cover gasket 113 provides a seal between the chamber cover 75 and the top portion of the drying chamber 40. A seal groove 112 is formed in the top portion of the drying chamber 40 that directly opposes the chamber cover 75. The cover gasket 113 is set into the seal groove 112, and projects slightly above the top surface of the drying chamber 40, thereby ensuring a tight seal when the chamber cover 75 is secured. Due to the pressure in the drying chamber 40, the cover gasket 113 must be made from a material that is inert to the fluids used in the drying chamber 40 and must be able to withstand the chamber pressure without deformation. Preferably, the cover gasket 113 comprises Teflon™ or an equivalent material.

Figure 7:
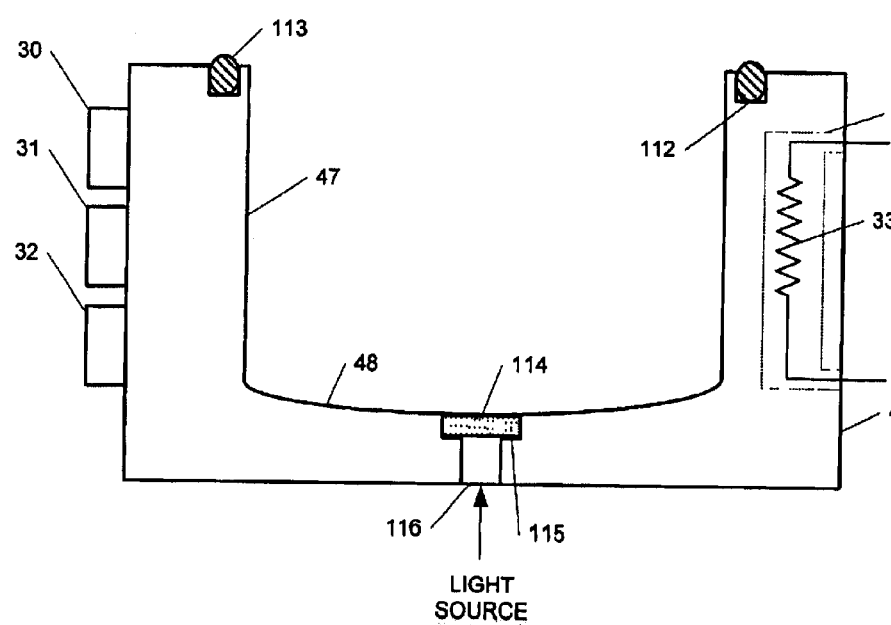
FIG. 7 illustrates a cross-sectional view of the drying chamber along lines II—II showing the temperature sensor, the heat sensor, the cool sensor and the heater.

Referring to FIG. 7, the cross-section of the drying chamber 40 along lines II—II is illustrated in more detail. The drying chamber 40 also has at least one heater 33 mounted in a cavity 34 in the drying chamber wall 47 to heat the transitional fluid above the critical point. Preferably, the heater 33 is a wirewound resistance heater that is controlled by the computer system 99.

A temperature sensor (not shown) is mounted in the wall of the drying chamber 40 is connected to a temperature gauge 23 to provide an indication of the drying chamber temperature. In addition, three other temperature sensors are mounted on the drying chamber wall 47. A heat sensor 31 (normally closed) opens when the temperature in the drying chamber 40 reaches a predetermined level and the opening of the heat sensor 31 is monitored by the computer system 99. Preferably, the beat sensor 31 is a thermostatic sensor and opens when the drying chamber temperature exceeds 42° C. A cool sensor 32 (normally closed) opens when the temperature in the drying chamber 40 drops past a predetermined level and the opening of the cool sensor 32 is monitored by the computer system 99. Preferably, the cool sensor 32 is a thermostatic sensor and opens when the drying chamber temperature is less than 5° C. Finally, the safety sensor 30 ensures that the heater 33 does not raise the drying chamber temperature past a predetermined safety level. If the drying chamber temperature exceeds the predetermined safety level, all power to the heater 33 is cut off. Preferably, the safety sensor 30 is a thermostatic sensor and opens when the drying chamber temperature exceeds 50° C.

Figure 8:
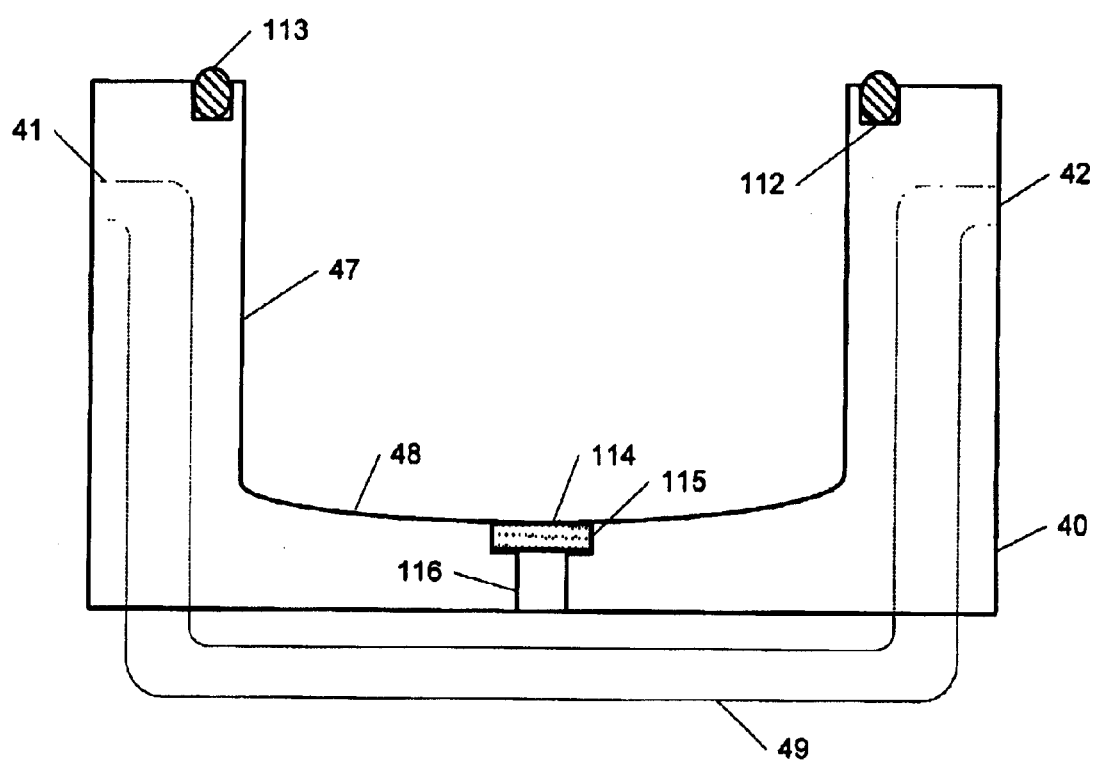
FIG. 8 illustrates a cross-sectional view of the drying chamber along lines III—III showing the cool inlet and the cool outlet.

Referring to FIG. 8, the cross-section of the drying chamber 40 along lines III—III is illustrated in more detail. A cooling fluid is circulated to cool the drying chamber wall 47 by passing into the cool inlet 41 through the walls of the drying chamber and the connecting line 49 and out through the cool outlet 42. Preferably, liquid carbon dioxide is used as a cooling fluid. The cooling fluid cools the drying chamber 40 by adiabatic cooling, which is turned on and off automatically via thermostatic controls. The fittings and tubing through which the cooling fluid flows is preferably stainless steel. In order to protect the integrity of the specimen, all external and internal surfaces of the critical point drying apparatus 1 are both chemically and moisture resistant, and all internal surfaces are inert to the intermediary and transitional fluids, such as liquid carbon dioxide and ultra-pure alcohol. In addition, all internal and external surfaces are grounded to guard against static discharge that is harmful to semiconductor wafers.

Figure 9:
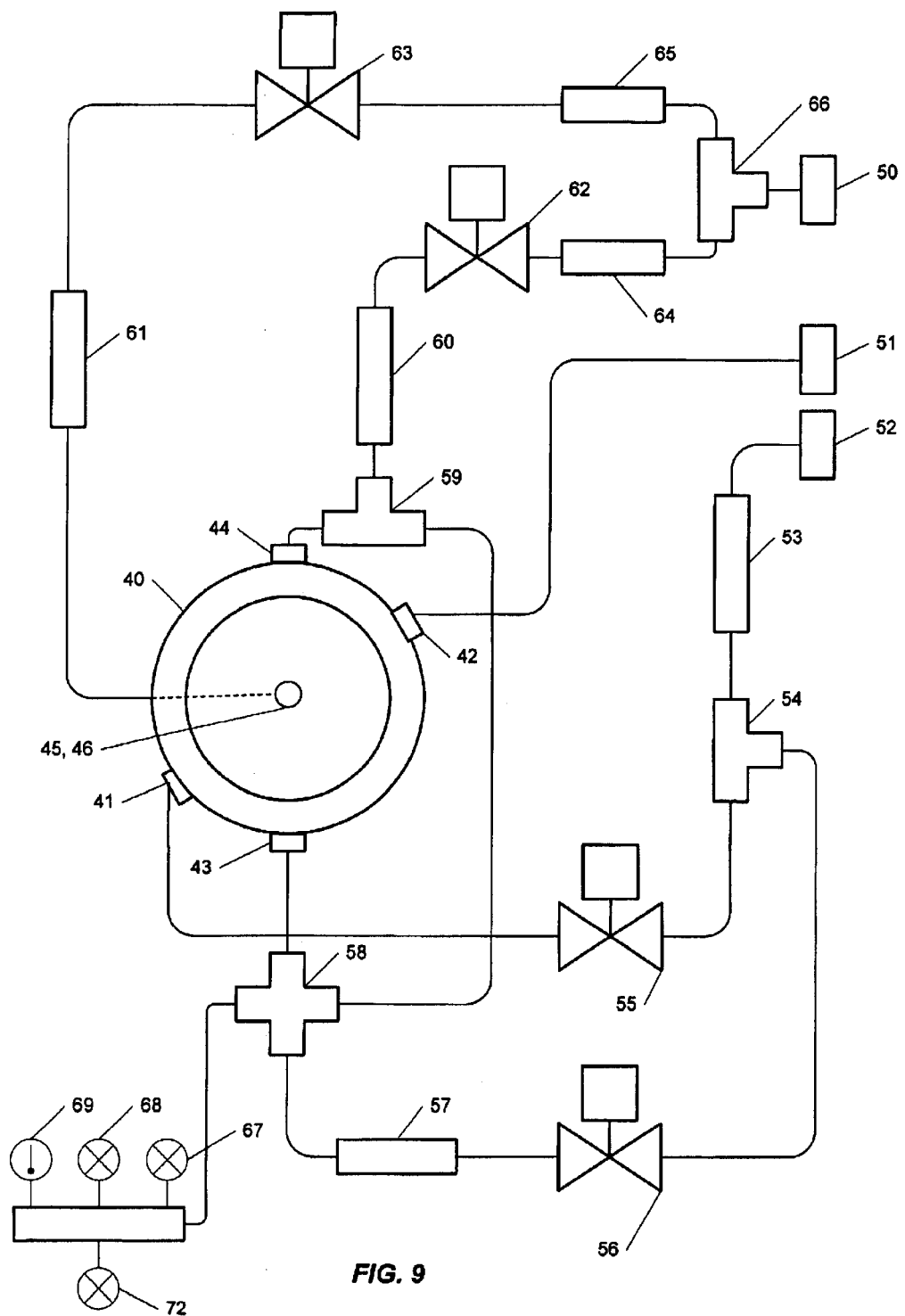
FIG. 9 illustrates the various valves and connection lines for the routing of cooling fluid and transitional fluid through the critical point drying apparatus.

Referring to FIG. 9, a schematic diagram showing the flow of fluids through the drying chamber 40 and the various control valves is illustrated. The transitional fluid is also utilized to cool the drying chamber 40 through the cooling circuit shown. The transitional fluid, preferably liquid carbon dioxide, is provided at the inlet port 52 and then flows through a filter assembly 53 to the 3-way tee 54. The filter assembly 53 removes any particulate matter from the transitional fluid prior to entering the various valves of the critical point drying apparatus 1. Preferably, the filter assembly 53 is a stainless steel filter that removes particulate up to 0.5 microns in diameter in order to protect the specimen in the drying chamber 40, as well as the critical point drying apparatus valves. Preferably, all tubing, fittings, valves, etc. are stainless steel. In addition, a rupture disc that will burst and evacuate the system in case of an undesirable rise in pressure protects the entire pressure system (not shown).

The transitional fluid is then piped to a pair of computer system controlled solenoid operated valves: the fill valve 56 and the cool valve 55. The fill valve 56 and cool valve 55 also comprise metering valves to control the flow rate of fluids through the valves.

When the computer system 99 energizes the cool valve 55 solenoid, the cool valve 55 supplies the transitional fluid through the metering valve to the drying chamber 40 at the cool inlet 41. The metering valve regulates the flow of transitional fluid through the wall of the drying chamber. When the cool valve 55 is energized, the transitional fluid flows out from the cool valve 55 and through the connection line to the drying chamber 40, wherein the transitional fluid is evaporated and ducted throughout the wall of the drying chamber 40. The flow is from the cool inlet 41 through the wall of the drying chamber 40 to the cool outlet 42. The warmed vaporized cooling fluid is ducted out of the critical point drying apparatus 1 at the cool port 51. If a closed loop refrigeration system is used, the cooling fluid is cycled back to a refrigeration unit. The closed loop system may use a refrigerant other than liquid carbon dioxide, such as Freon™.

When the computer system 99 energizes the fill valve 56, transitional fluid flows into the fill inlets 43,44 to fill or purge the drying chamber 40. When the drying chamber 40 is being filled with the transitional fluid, the computer system 99 energizes the fill valve 56, and transitional fluid flows from the fill valve 56, through a check valve 57, a 4-way tee 58 and into the drying chamber 40 through the fill inlets 43,44. The fill inlets 43,44 are coupled to each other through 4-way tee 58 and 3-way tee 59. The in-line check valve 57 protects the fill valve from any backflow to the drying chamber.

A connection line from the 4-way tee 58 is connected to a high-pressure sensor 67, a low-pressure sensor 68 and a pressure gauge 69. The low-pressure sensor 68 opens when the chamber pressure drops below a predetermined low pressure point, and the opening of the low-pressure sensor 68 is monitored by the computer system 99. An acceptable range for the predetermined low pressure point is from 100 to 600 psi. Preferably, the predetermined low pressure point is 400 psi.

The high-pressure sensor 67 opens when the chamber pressure exceeds a predetermined high pressure point, and the opening of the high-pressure sensor 67 is monitored by the computer system 99. An acceptable range for the predetermined high pressure point is from 1175 and 1600 psi. Preferably, the predetermined high pressure point is 1200 psi.

A pressure relief valve (not shown) is also connected to the pressure sensors. The pressure relief valve will release the pressure from the critical point drying apparatus 1 when the drying chamber pressure exceeds a predetermined limit. The pressure relief valve is heated and the heating of the pressure relief valve is thermostatically controlled independent of the computer system 99. An acceptable range for the pressure relief valve is from 1200 to 1600 psi. Preferably, the pressure relief valve opens at 1250 psi.

A rupture disc 72 is also connected to the pressure sensors. The rupture disc 72 acts as an additional safety feature and is set to burst when the drying chamber pressure goes above a predetermined limit. An acceptable range for the rupture disc 72 is from 1900 to 3000 psi. Preferably, the rupture disc 72 ruptures at 2100 psi.

When the intermediary fluid is to be purged from the drying chamber 40, the computer system 99 commands the purge valve 63 to open. The purge valve 63 is a solenoid valve. The intermediary fluid is forced from the drying chamber 40 through the purge outlets 45,46 in the drying concave surface 48 and into the connection line through a filter assembly 61, which is connected to the purge valve 63. The purge valve 63 is heated to prevent the purge valve 63 from freezing when the transitional fluid or the intermediary fluid passes through the purge valve 63. The heating of the purge 63 valve is thermostatically controlled independent of the computer system 99. The purge valve 63 also includes a metering valve to control the flow rate at which the transitional fluid or intermediary fluid is purged. Attached to the exiting end of the purge metering valve is a check valve 65 to prevent fluid backflow through the purge valve 63 into the drying chamber 40. The optional check valve 65 is connected to the purge outlet 50 by 3-way tee 66. The purged fluid exits the critical point drying apparatus 1 through the purge outlet 50. Throughout the entire purging process, the computer system 99 monitors the drying chamber temperature and keeps the drying chamber 40 below a predetermined temperature, preferably 5° C. or less.

The cycle time for executing a purge of the intermediary fluid from the drying chamber 40 is controlled by the computer system 99. Preferably, the purge time is adjusted by a purge timing control 25 that is located on the housing 24 of the critical point drying apparatus 1. After the purge cycle for the purging of the intermediary fluid is complete, the computer system 99 closes the purge valve 63 and allows the fill valve 56 to continue filling the drying chamber 40 with transitional fluid. This ensures the transitional fluid fills the drying chamber 40 completely. The computer system 99 then advances the drying chamber 40 into the heating cycle.

The computer system 99 activates the heater 32 to raise the transitional fluid to its critical point pressure and critical point temperature, thereby reaching critical point equilibrium. Preferably, the heater 32 raises the drying chamber temperature to at least 311° C. or greater, which, in turn, causes the temperature and pressure of the transitional fluid to reach its critical point temperature and pressure.

After the computer system 99 has determined that the specimen has been at the critical point equilibrium for a sufficient amount of time, the computer system 99 commands the bleed valve 62 to open, thereby allowing the transitional fluid to exhaust out of the drying chamber 40 and exit the critical point drying apparatus 1 through the purge outlet 50. The bleed valve 62 is a solenoid valve. When the transitional fluid is exhausted, it flows from the drying chamber 40 through a filter assembly 60 into the bleed valve 62 and then into the check valve 64. The check valve 64 prevents backflow from backing through the bleed valve 62 into the drying chamber 40. The optional check valve 64 is connected to the purge outlet 50 through 3-way tee 66. The bleed valve 62 also comprises a metering valve to control the bleed rate. Preferably, the metering valve allows the system pressure to decrease at a rate of 100 psi/minute. This bleed rate prevents the transitional fluid from recondensing. In addition, the bleed valve 62 is thermostatically heated to prevent the bleed valve 62 from freezing as the transitional fluid flows through it. During the bleed process, the computer system 99 maintains the drying chamber temperature at 31° C. or above. This temperature level prevents recondensation on the specimen. When the drying chamber pressure is reduced to 400 psi, the computer system 99 turns off the heater 32 and switches from bleed to vent mode. The computer system 99 commands the bleed valve 62 to close and the purge valve 63 to open. This returns the drying chamber to atmospheric pressure quicker.

Figure 9A:
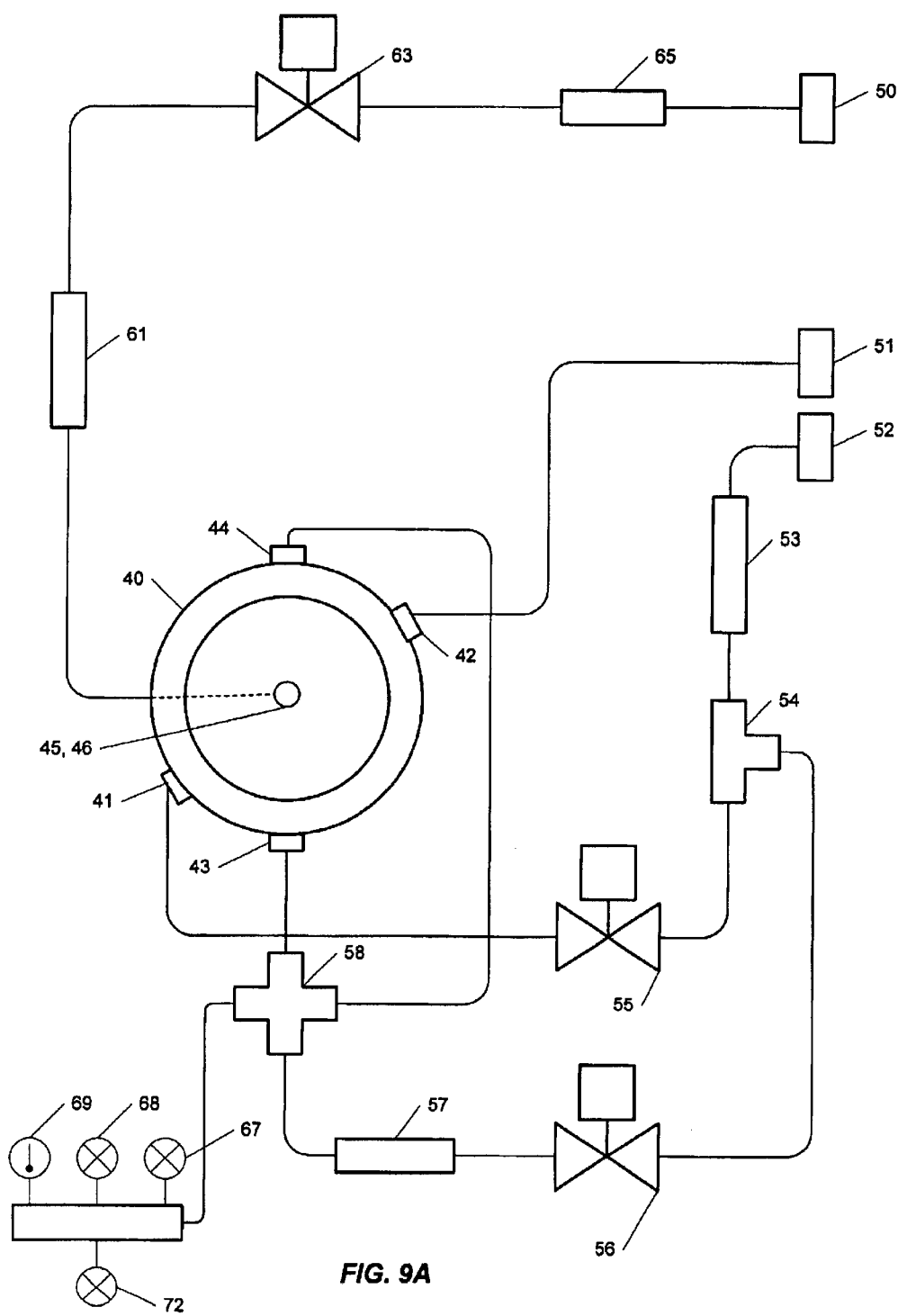
FIG. 9A illustrates another embodiment of the various valves and connection lines for the routing of cooling fluid and transitional fluid through the critical point drying apparatus.

Referring to FIG. 9A, a schematic diagram showing the flow of fluids through the drying chamber 40 and the various control valves is illustrated. This is an embodiment of the present invention that uses only three valves to control the flow of fluids through the drying chamber 40. In the embodiment depicted in FIG. 9A, the filter assembly 60, the bleed valve 62, the check valve 64 and the three-way tee 66 are eliminated. The purge port 50 is connected to the purge valve 63 through the check valve 65. The use of the check valve 65 is optional. The fill inlet 44 is directly connected to the 4-way tee 58. After the computer system 99 has determined that the specimen has been at the critical point equilibrium for a sufficient amount of time, the computer system 99 conmmands the purge valve 63 to open, thereby allowing the transitional fluid to exhaust out of the drying chamber 40 and exit the critical point drying apparatus 1 through the purge outlet 50. The purge valve 63 is thermostatically heated to prevent the purge valve 63 from freezing as the transitional fluid flows through it. During the bleed process, the computer system 99 maintains the drying chamber temperature at 31° C. or above. This temperature level prevents recondensation on the specimen. When the drying chamber pressure is reduced to 400 psi, the computer system 99 turns off the heater 32 and switches from bleed to vent mode.

Figure 10:
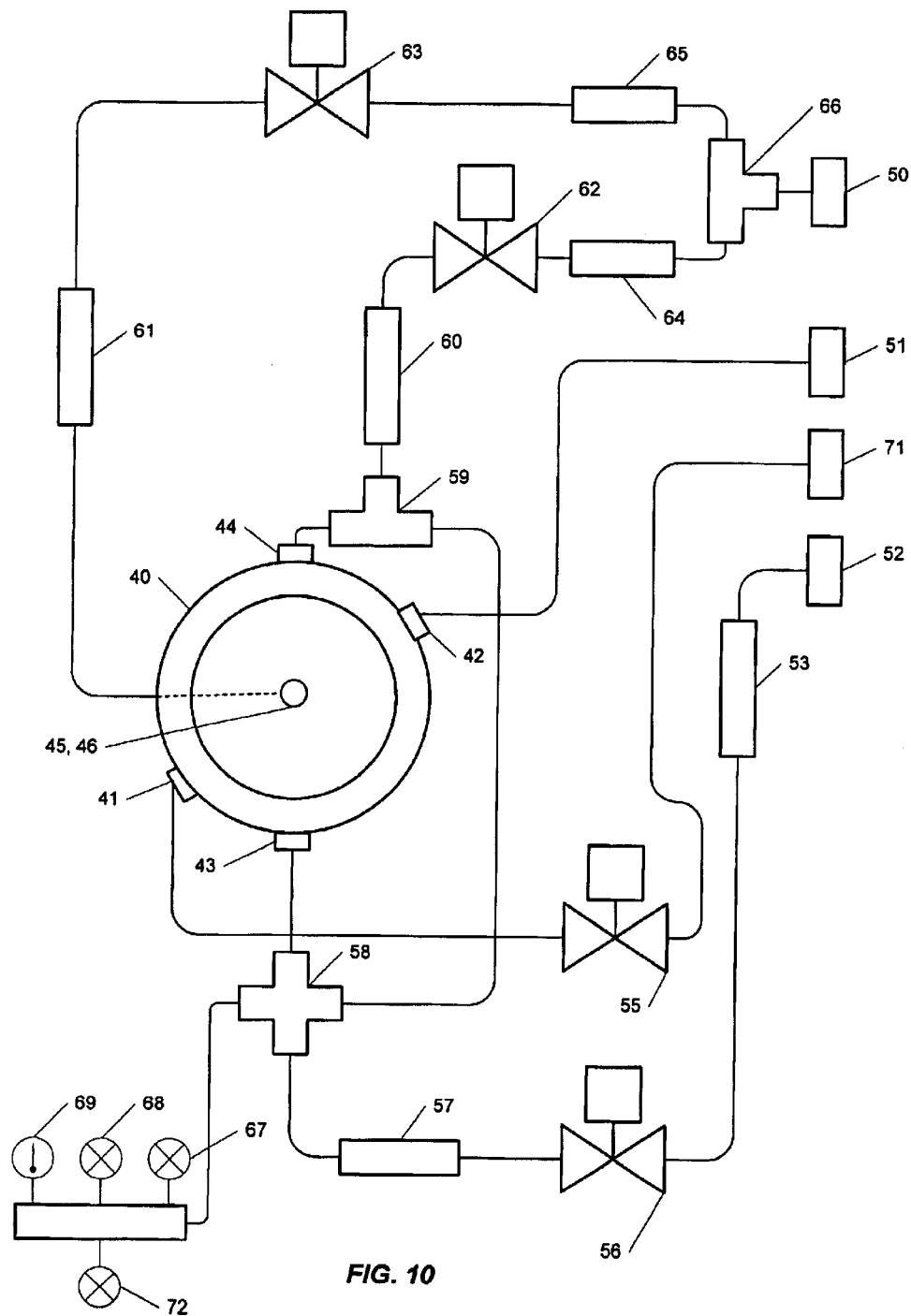
FIG. 10 illustrates the various valves and connection lines for the routing of cooling fluid and transitional fluid through a critical point drying apparatus that is connected to a closed loop refrigeration system.

Referring to FIG. 10, in another aspect of the invention, the drying chamber 40 can be cooled using a closed loop refrigeration system. The closed loop system is coupled to the drying chamber 40 and allows the drying chamber 40 to be cooled without blasting liquid carbon dioxide through the drying chamber 40. This feature of the present invention provides for savings on the amount of carbon dioxide that is used during a specimen drying sequence. In addition, the closed loop system may use a refrigerant other than liquid carbon dioxide, such as Freon™. Cooling fluid enters the critical point drying apparatus 1 through cool supply port 71 and is piped to the cool valve 55. A common supply for cooling fluid and transitional fluid is not used.

Figure 10A:
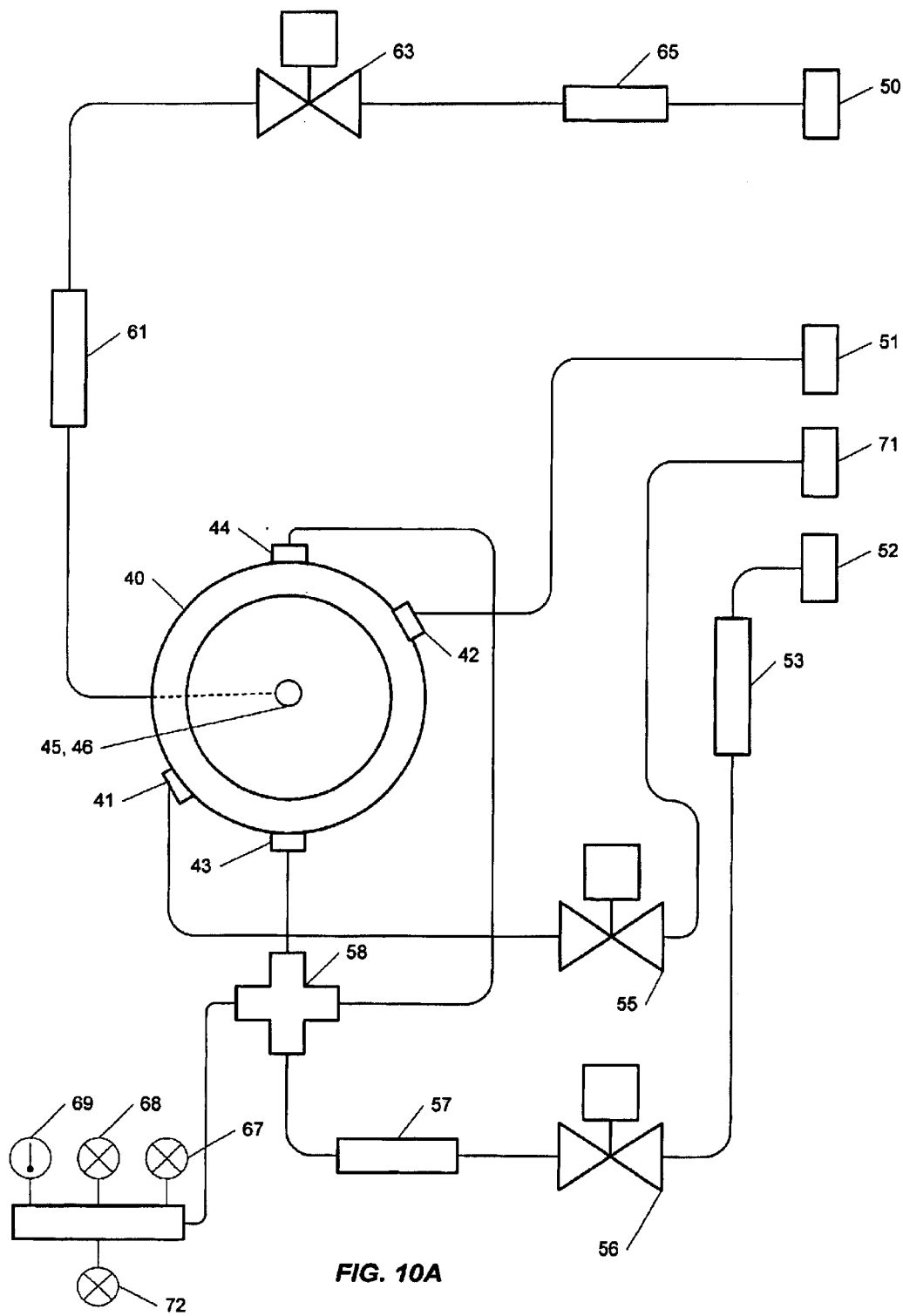
FIG. 10A illustrates another embodiment of the various valves and connection lines for the routing of cooling fluid and transitional fluid through a critical point drying apparatus that is connected to a closed loop refrigeration system.

Referring to FIG. 10A, in another embodiment of the present invention, the drying chamber 40 can be cooled using a closed loop refrigeration system with only three valves to control the flow of fluids through the drying chamber 40. In the embodiment depicted in FIG. 10A, the filter assembly 60, the bleed valve 62, the check valve 64 and the three-way tee 66 are eliminated. The purge port 50 is connected to the purge valve 63 through the check valve 65. The use of the check valve 65 is optional. The fill inlet 44 is directly connected to the 4-way tee 58. After the computer system 99 has determined that the specimen has been at the critical point equilibrium for a sufficient amount of time, the computer system 99 commands the purge valve 63 to open, thereby allowing the transitional fluid to exhaust out of the drying chamber 40 and exit the critical point drying apparatus 1 through the purge outlet 50. The purge valve 63 is thermostatically heated to prevent the purge valve 63 from freezing as the transitional fluid flows through it. During the bleed process, the computer system 99 maintains the drying chamber temperature at 31° C. or above. This temperature level prevents recondensation on the specimen. When the drying chamber pressure is reduced to 400 psi, the computer system 99 turns off the heater 32 and switches from bleed to vent mode.

Figure 11:
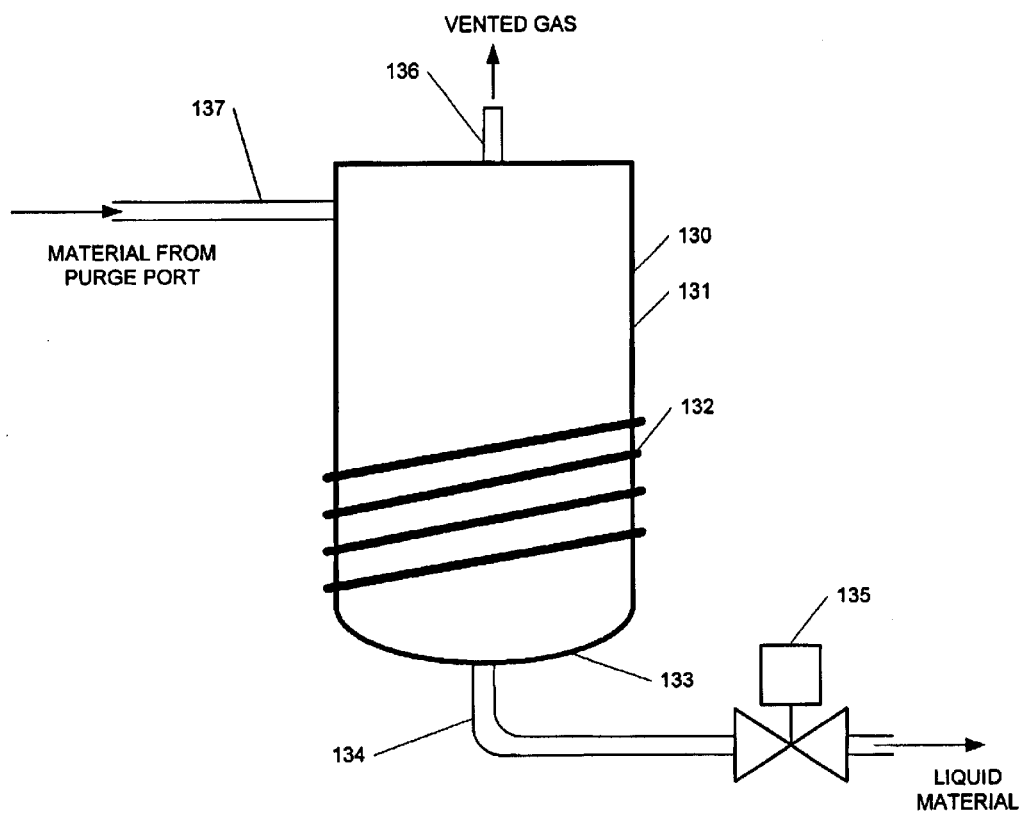
FIG. 11 illustrates a side view of the collector condenser.

Referring to FIG. 11, a condenser collector 130 allows the intermediary fluid (i.e., the dehydrating fluid) to be purged from the drying chamber 40 in a safer and more controlled manner. The condenser collector 130 is connected to the purge port 50. Preferably, methyl alcohol or ethyl alcohol is used as intermediary fluid for the specimen drying process, although these fluids are relatively toxic. When the intermediary fluid is purged from the drying chamber 40 under pressure, the intermediary fluid often exits the drying chamber 40 in a frozen state. The condenser collector 130 transforms the intermediary fluid back into a liquid state so that it may be drained from the condenser collector 130 easily. Preferably, the condenser collector 130 uses a thermostatically controlled heated reservoir 131 with a concave bottom portion 133. The drain line 134 the condenser collector 130 is located on the low point of the concave bottom portion 133 and a drain valve 135 regulates the exit flow of the material.

The outgoing intermediary fluid, both in its gaseous state and frozen state, enters through a reservoir inlet 137 on the upper portion of the reservoir 131. The gas is allowed to exit through the gas vent 136 of the reservoir 131, while the frozen portions of the intermediary fluid remain in the reservoir 131. The heater 132 then warms the reservoir 131 and the frozen intermediary fluid returns to a liquid state and is then drained from the reservoir 131. Preferably, the condenser collector 130 can be constructed from stainless steel, brass or polyvinyl chloride. The reservoir 131 of the condenser collector 130 is insulated to prevent condensation from developing on the surfaces of the reservoir 131.

Figure 12:
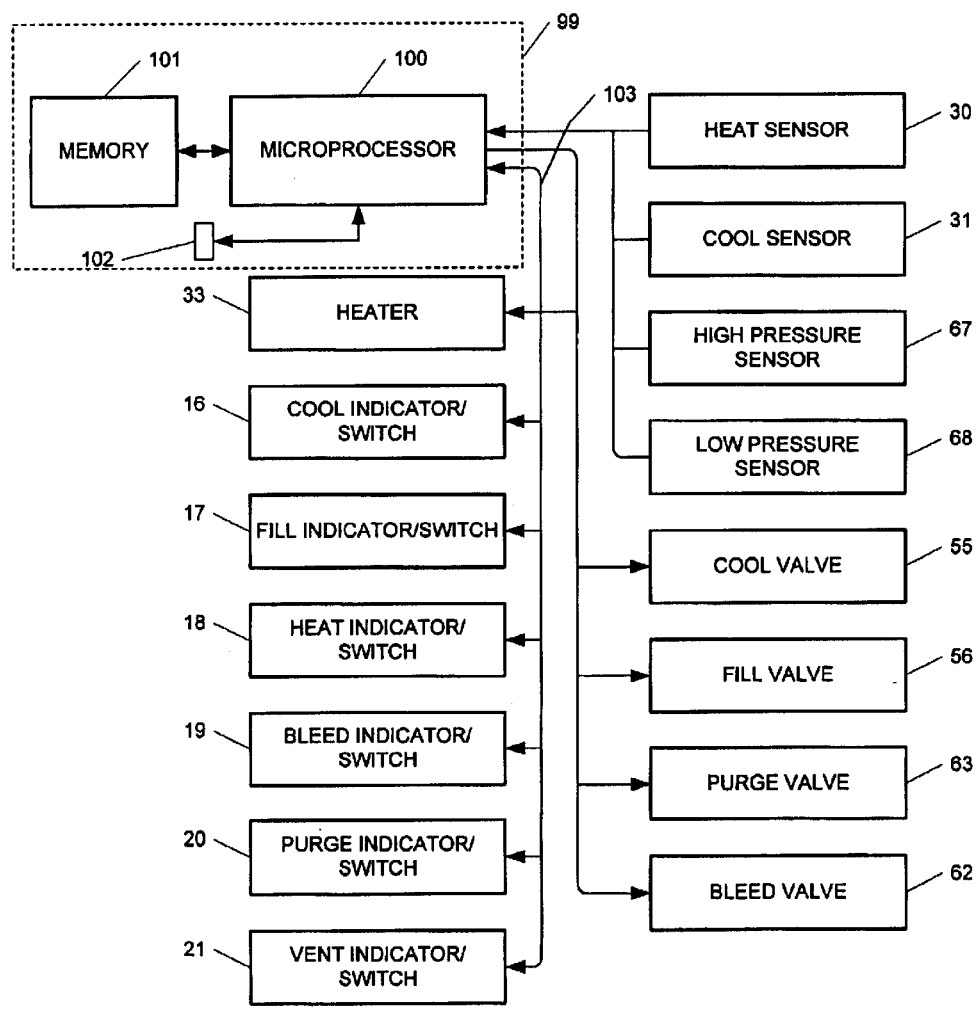
FIG. 12 illustrates the data flow paths between the computer system and the various valves and sensors.

Referring to FIG. 12, the computer system 99 with software that is adapted to perform critical point drying techniques when coupled to a critical point drying apparatus 1 will now be described in summary fashion. As described above, the computer system 99 includes a processor for executing software instructions adapted to enable the computer to control a critical point drying chamber and its associated valve and heaters. The computer system 99 includes a memory 101 that stores the software instructions adapted to enable the computer system 99 to control the drying chamber 40 and associated valves. The computer system 99 also comprises an I/O port that allows the computer system 99 to be re-programmed and to upload/download data. As shown in FIG. 12, the computer system 99 receives inputs from the temperature and pressure sensors through the data lines 103. Commands to open or close the cool valve 55, the fill valve 56, the bleed valve 62 and the purge valve 63 are sent over the data lines 103. Finally, the computer system 99 receives commands from the indicator switches on the housing 24 that indicate the various modes, and the computer system 99 also lights the appropriate indicator switch to inform the operator which mode is currently being executed.

Figure 13A:
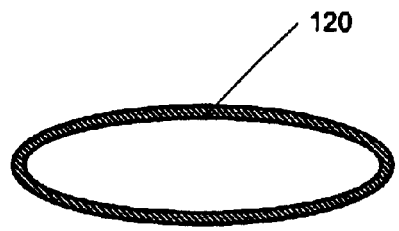
FIG. 13A illustrates a view of the spacer ring.
Figure 13B:
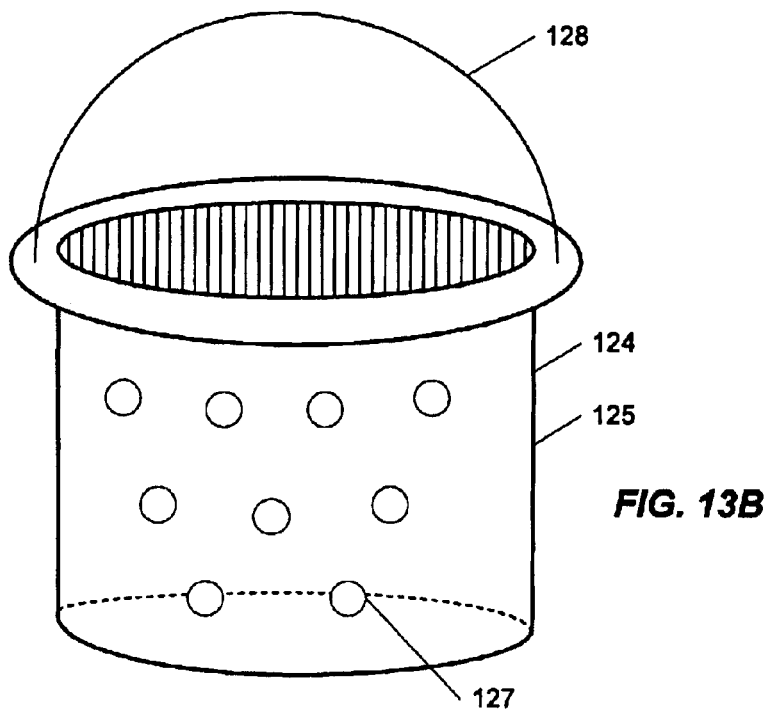
FIG. 13B illustrates a side view of the wafer holder.
Figure 13C:
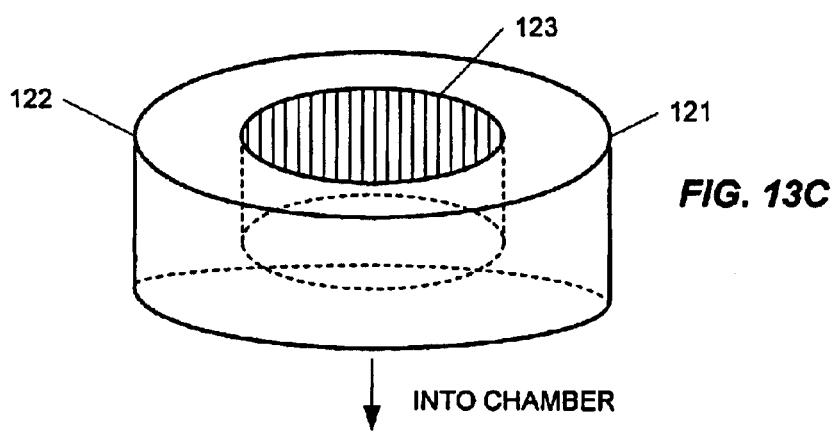
FIG. 13C illustrates a side view of the chamber insert for the drying chamber.

Referring to FIGS. 13A-13C, when the critical point drying apparatus 1 will be used to process semiconductor wafers, the drying chamber must be outfitted with a mechanism to hold the semiconductor wafer in a suspended position so that the drying process can be achieved. The critical point drying apparatus 1 that are designed to process semiconductor wafers are outfitted with a wafer holder 124, a spacer ring 120 and a chamber insert 121. Preferably, these components come in different sizes to accommodate different wafer sizes, and are made out of Teflon™ or an equivalent material.

The spacer ring 120 is placed in the bottom of the appropriate wafer holder 124, then a semiconductor wafer can be placed on top, and another spacer ring 120 can then be put in place so that another semiconductor wafer can be added. This method of suspended stacking allows multiple wafers to be successfully processed during one run.

Since semiconductor wafers come in several different sizes, there are several different size wafer holders 124. When a smaller wafer holder 124 is needed to process a semiconductor wafer, a chamber insert 121 is used to hold the wafer holder 124 in place and reduce the amount of transitional fluid used. For example, if the drying chamber 40 has a six and one half inch internal diameter and the operator wishes to process a four inch wafer, then a chamber insert 121 is put into place (having a six inch outer diameter with cavity 123 that has a four inch internal diameter). The wafer then is placed in the four-inch wafer holder 124 that is placed inside the chamber insert 121.

The wafer holder 124 is comprised of a body 125 and a handle 128. The body 125 has a plurality of fluid holes 127 that allow the transitional fluid to reach the semiconductor wafers stacked inside the body 125.

Figure 14:
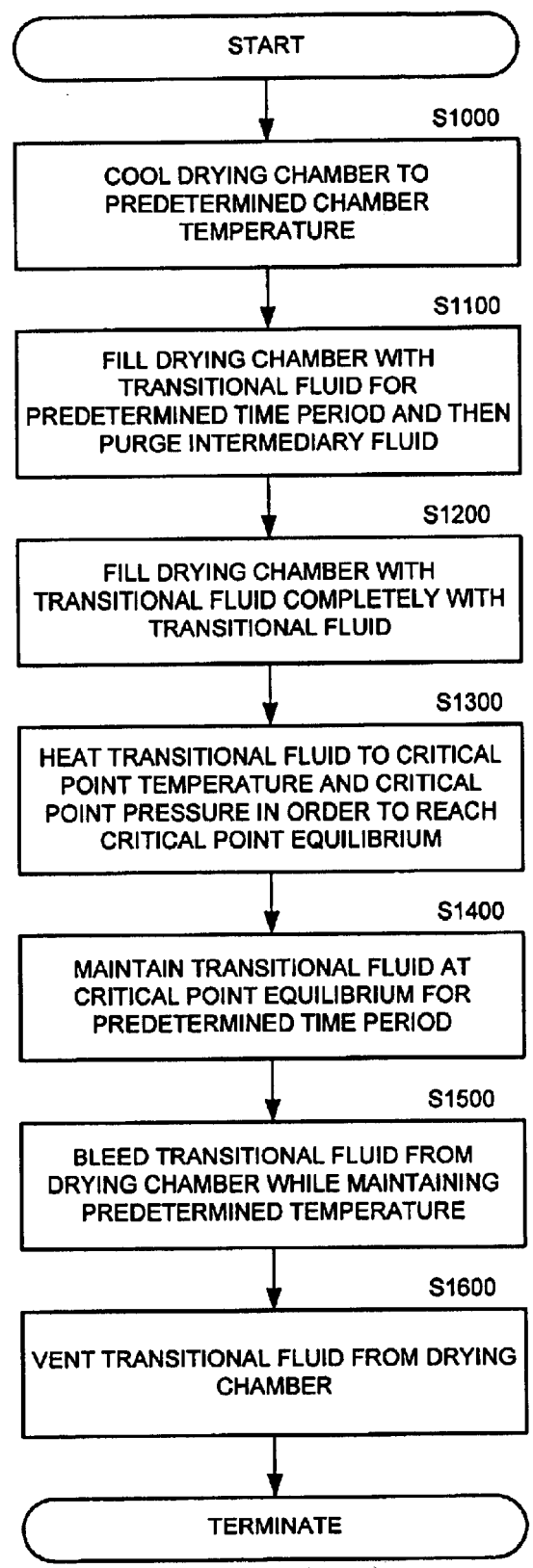
FIG. 14 illustrates the process steps executed by the computer system when controlling a critical point drying process in the drying chamber.

Referring to FIG. 14, as described above, these software instructions can be resident on the microprocessor 100 or stored on a separate memory 101. At Step S1000, the computer system 99 executes software instructions to cool the drying chamber 40 to a first chamber temperature. At S1100, the computer system 99 executes software instructions to fill the drying chamber 40 with a transitional fluid having a critical point temperature and critical point pressure while maintaining the drying chamber 40 at the first chamber temperature, and then the computer system 99 executes software instructions to purge the intermediary fluid from the drying chamber 40. At S1200, the computer system 99 executes software instructions to fill to ensure the drying chamber 40 is completely filled. At S1300, the computer system 99 executes software instructions to activate a heater 32 to raise the transitional fluid to its critical point pressure and critical point temperature, thereby reaching critical point equilibrium. At S1400, the computer system 99 executes software instructions to maintain the transitional fluid at the critical point equilibrium for a second time period. At S1500, the computer system 99 executes software instructions to bleed the transitional fluid from the drying chamber 40 while maintaining the drying chamber 40 at the second chamber temperature and allowing the drying chamber pressure to drop. At S 1600, the computer system 99 executes software instructions to vent the transitional fluid from the drying chamber.

The software instructions adapted to enable the computer system 99 to control the drying chamber 40 and the associated valve assemblies will now be described in greater detail.

Figure 15A:
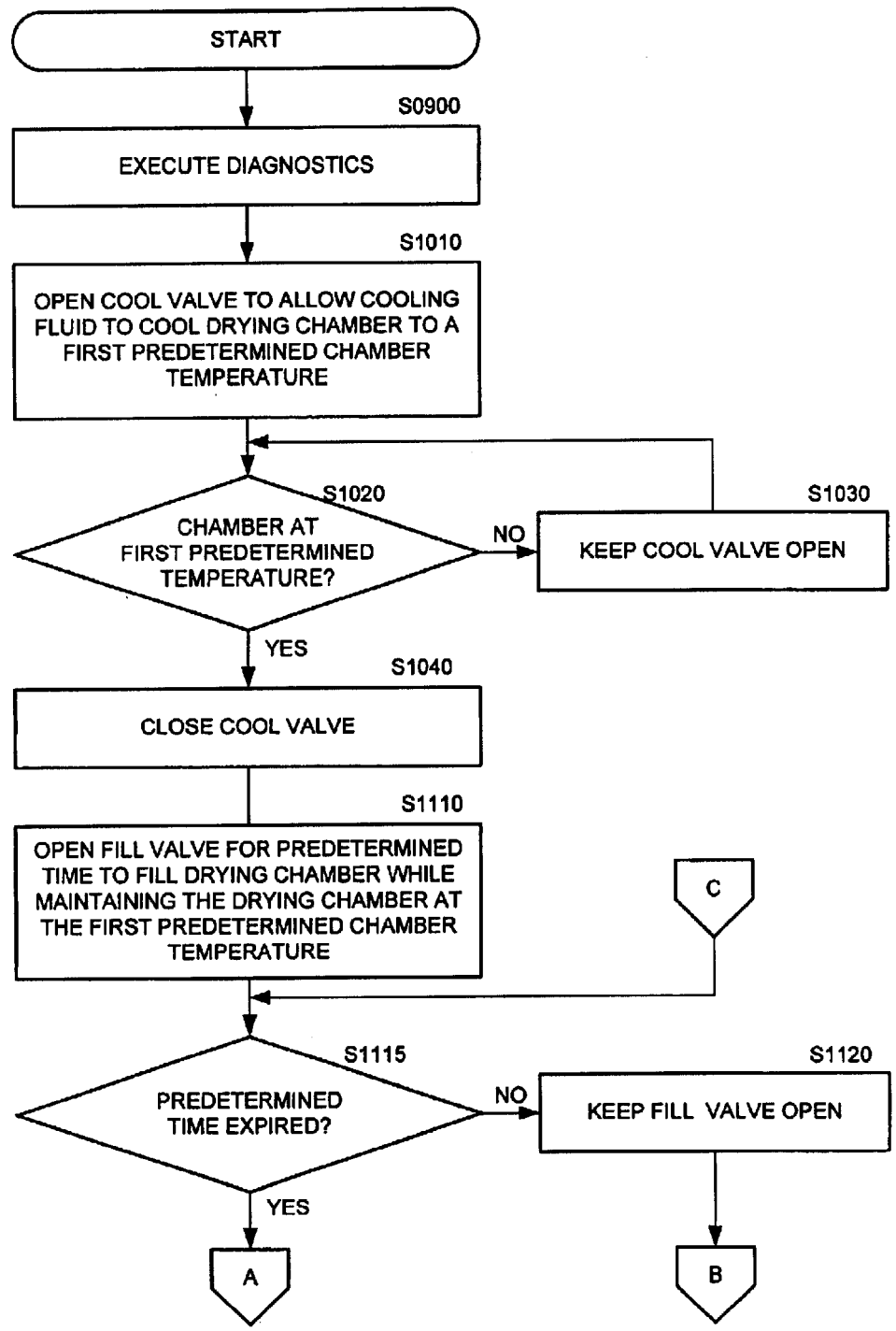
FIGS. 15A-15F illustrate the process steps, in more detail, executed by the computer system when controlling a critical point drying process within the drying chamber.

Referring to FIG. 15A, if commanded to by the operator, the computer system 99 executes diagnostic routines to determine if the critical point drying apparatus 1 is in working order. These diagnostics are described in greater detail below.

Next, the software instructions executed by the computer system 99 cool the drying chamber 40 to a predetermined value. As described above, at S1010, the computer system 99 commands the cool valve 55 to open, thereby allowing the cooling fluid to flow from the inlet port 52, through the cool valve 55 and into the drying chamber walls, thereby cooling the drying chamber 40 to the desired temperature level. As described above, by commanding the cool valve 55 to open, a cooling fluid flows around the drying chamber and evaporates in a heat exchange relationship with the drying chamber 40. At S1020–1040, a determination is made whether the drying chamber 40 has reached the desired temperature. If not, the cool valve remains open.

After the specimen has been placed in the drying chamber 40 immersed in an intermediary fluid and the chamber cover 75 secured, at S1110, the computer system 99 commands the fill valve 56 to open, thereby allowing the transitional fluid to flow into the interior of the drying chamber 40. This is known as the fill mode and the computer system 99 allows the transitional fluid to flow into the drying chamber 40 for a preset amount of time. At the expiration of the preset time period, the computer system 99 commands the fill valve 56 to close. At S1115 to S1120, a determination is made if the preset time period has expired. If not, the fill valve remains open.

Figure 15B:
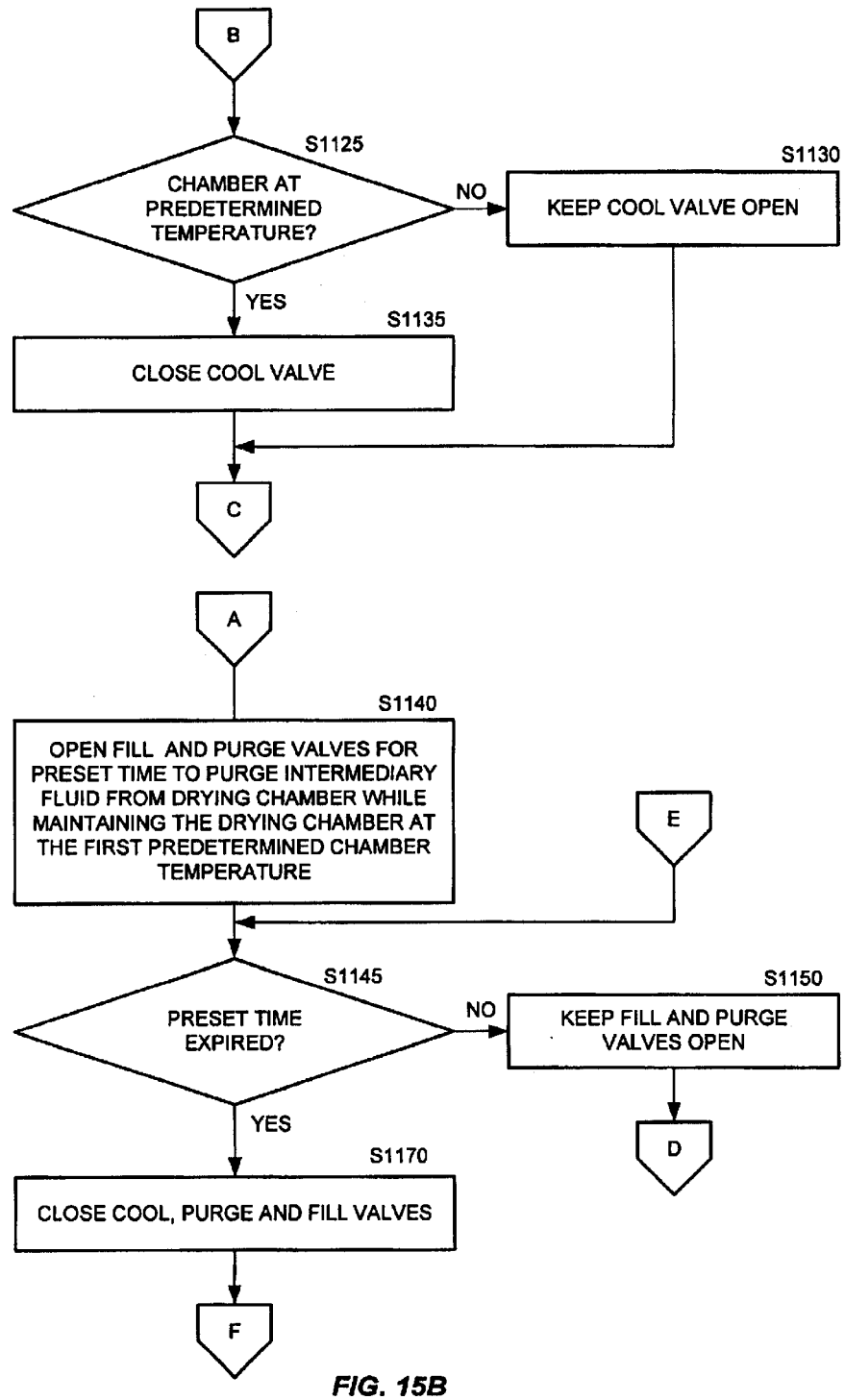

Referring to FIG. 15B, at S1125 to S1135, an additional determination is made whether the drying chamber 40 has remained at the desired temperature. If not, the cool valve is opened to cool the drying chamber 40.

Next, at S1140, the computer system 99 executes the software instructions for purging the intermediary fluid from the drying chamber 40. This is known as the purge mode, such that the transitional fluid completely fills the drying chamber 40 and purges the intermediary fluid from the treated specimen in the drying chamber 40.

Figure 15C:
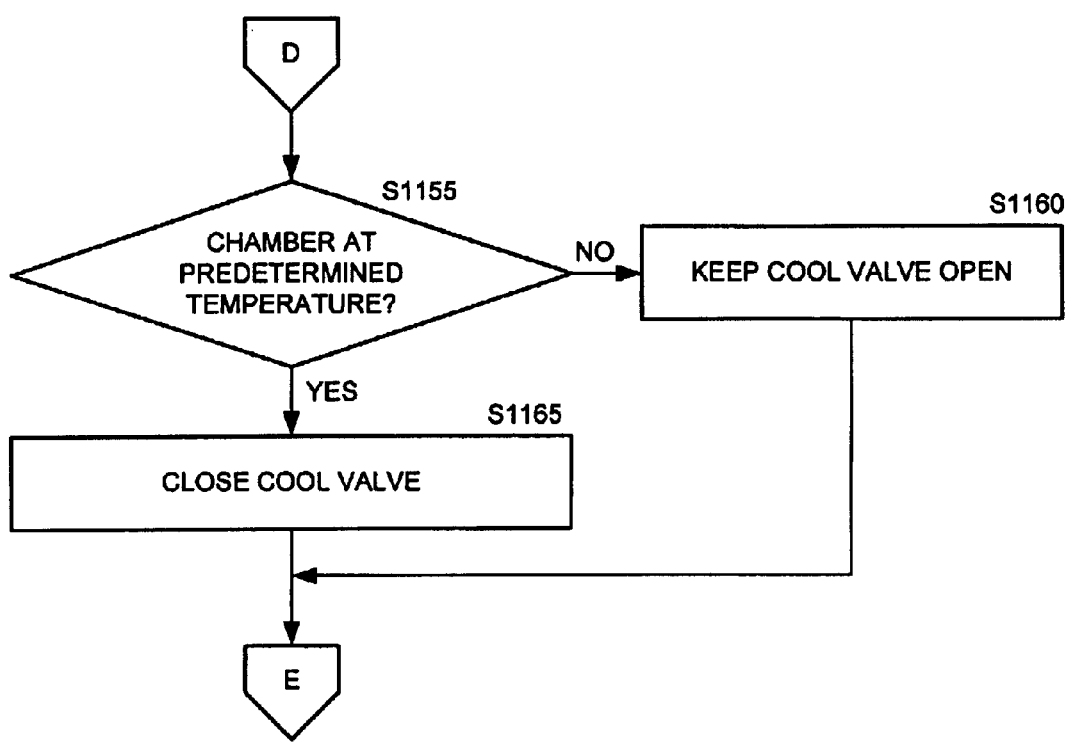

Referring to FIG. 15C, as shown by S1145 to S1150, the purging of the dehydrating fluid is controlled over a predetermined time period. As shown by S1155 to S1165, while the drying chamber 40 is being filled and purged, the computer system 99 maintains the drying chamber 40 at the predetermined temperature by controlling the cool valve 55. Preferably, the predetermined temperature is 0° C.

Referring to FIG. 15B, when the computer system 99 has determined that the purging cycle has reached the end of its time period, at S1170, the fill valve 56, the purge valve 63 and the cool valve 55 are closed. The drying chamber 40 now should be completely filled by the transitional fluid.

Figure 15D:
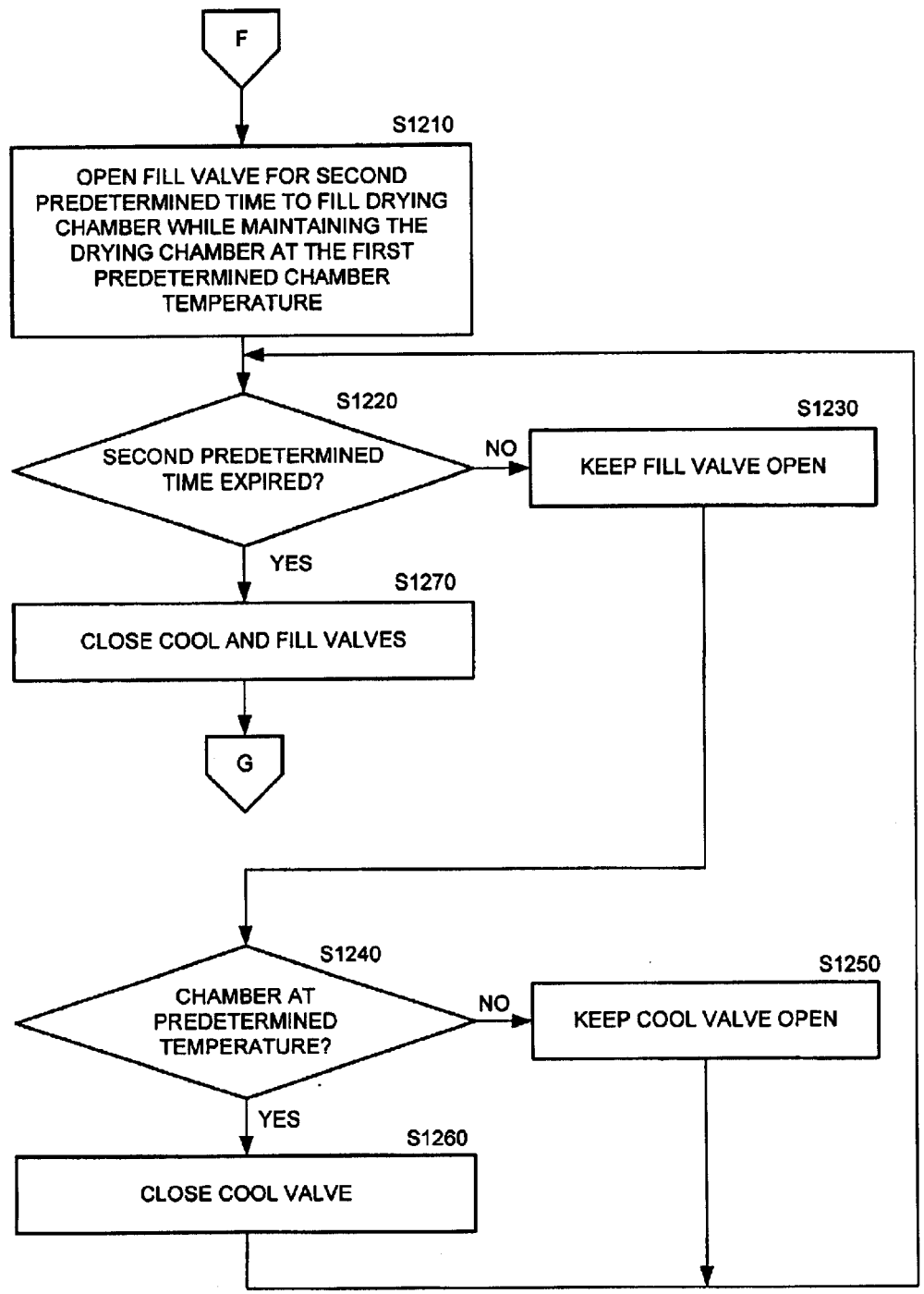

Referring to FIG. 15D, to ensure that the drying chamber 40 is completely filled, at S1210 to S1270, the computer system 99 executes software instructions that cycle back into the fill mode following the purging of the intermediary fluid. The cycling back into the fill mode ensures that the drying chamber 40 is completely filled by the transitional fluid. Therefore, the fill valve 56 is reopened by the computer system 99 to facilitate this task. During this fill, as shown by S1240 to S1260, the computer system 99 monitors the temperature and can activate the cool valve 55 if the drying chamber 40 needs to be cooled. Once complete, at S1270, all the valves are commanded to be closed.

Figure 15E:
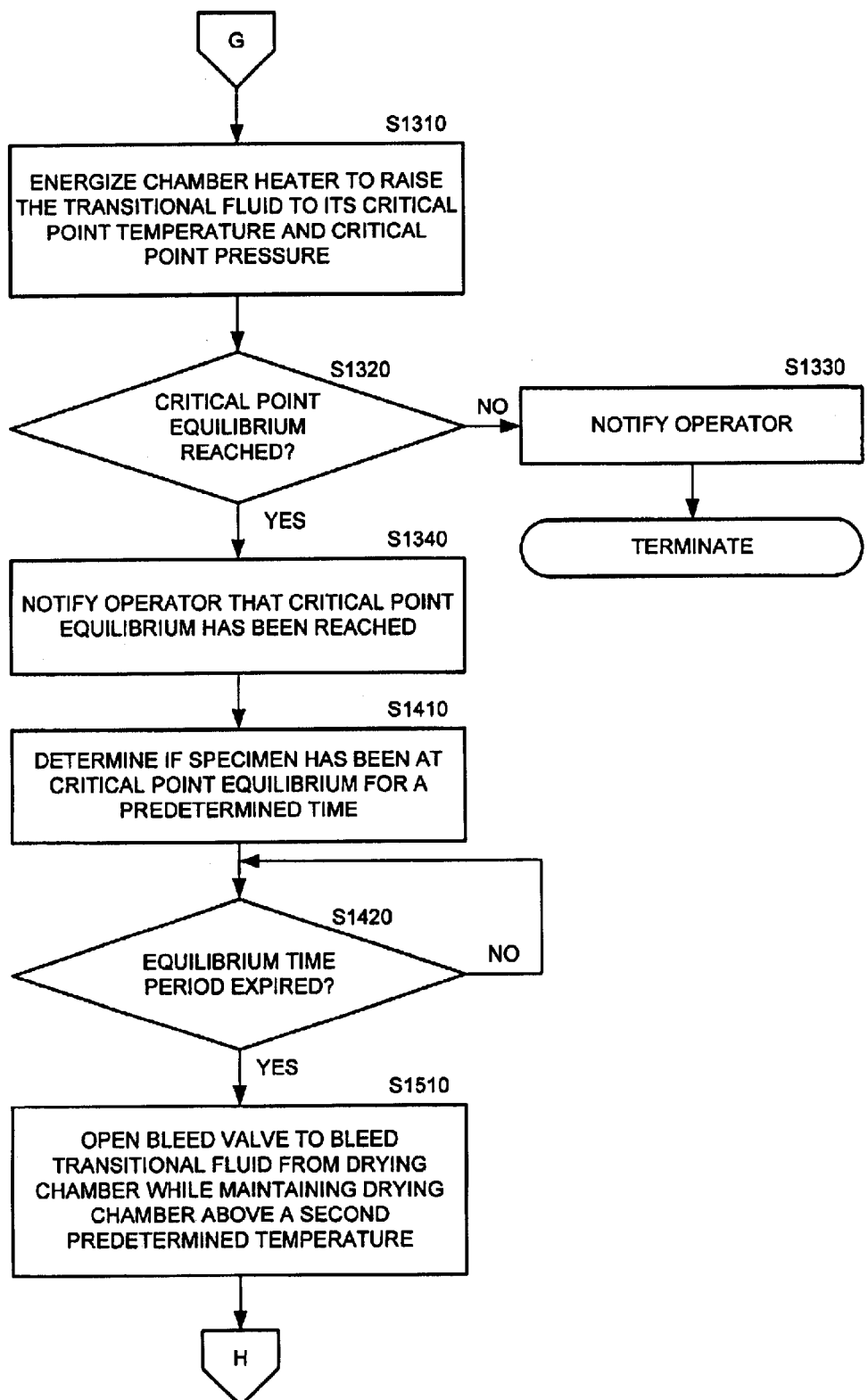

Referring to FIG. 15E, at S1310 to S1340, after the computer system 99 has completed the second chamber fill, the drying chamber 40 is heated to pressurize the transitional fluid to its critical point as well as raise its temperature to the critical point. The computer system 99 executes software instructions to activate the heater 33 mounted in the wall of the drying chamber. The computer system 99 monitors the temperature to ensure that the chamber temperature does not exceed a preset limit. Preferably, this temperature limit is between 48 and 500° C.

The software instructions also comprise instructions that command the computer system 99 to indicate to the operator that the pressure and temperature are above the critical point equilibrium. Preferably, the computer system 99 causes the heat LED 19 to flash thereby indicating that the specimens in the drying chamber 40 have reached the critical point equilibrium. The critical point equilibrium is maintained for a programmed amount of time. At S1320, if the heat thermostatic sensor 30 and the high pressure sensor 67 indicate that the critical point equilibrium has not been reached, the software instructions command the computer system 99 to indicate to the operator that there is a problem with the critical point drying sequence. At S1330, the computer system 99 will flash all the operation indication LEDs to indicate a problem with the critical point drying sequence. The operator is then allowed to press a switch to return to an earlier stage in the process at which point the computer system 99 will then take over and complete the drying sequence.

At S1410 to S1420, the computer system 99 executes software instructions to determine if the specimen has been at critical point equilibrium for a predetermined time period.

Figure 15F:
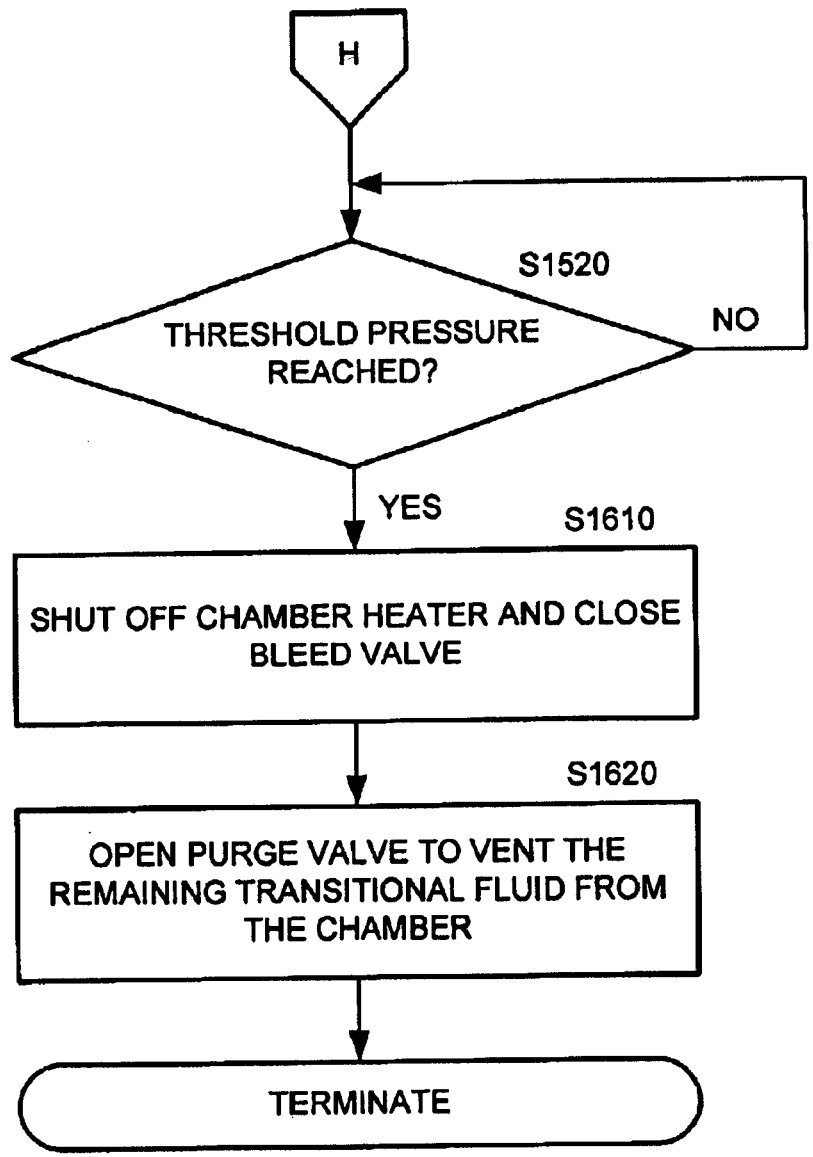

Referring to FIG. 15F, at S1510 to S1520, once the programmed amount of time at the critical point equilibrium has expired, the computer system 99 executes software instructions to bleed off the pressure in the drying chamber. The computer system 99 opens the bleed valve 62 and controls the bleeding of the pressure in the drying chamber 40 down between 100 and 600 psi while maintaining drying chamber temperature above 31° C. or above. Preferably, the low pressure threshold is 400 psi. When the computer system 99 is executing the bleed mode, the computer system 99 controls the bleeding of pressure from the drying chamber 40 in an even fashion. In dropping from 1100 psi to 400 psi, the computer system 99 allows the pressure to vent slowly from the drying chamber 40. In addition, the computer system 99 commands the heater 33 disposed on the drying chamber 40 to maintain the temperature of the drying chamber 40 at 31° C. or above.

For the three valve embodiments illustrated in FIGS. 9A and 10A, at S1510, once the programmed amount of time at the critical point equilibrium has expired, the computer system 99 executes software instructions to bleed off the pressure in the drying chamber. The computer system 99 opens the purge valve 63 and controls the bleeding of the pressure in the drying chamber 40 down between 100 and 600 psi while maintaining drying chamber temperature above 31° C. or above. Preferably, the low pressure threshold is 400 psi. When the computer system 99 is executing the bleed mode, the computer system 99 controls the bleeding of pressure from the drying chamber 40 in an even fashion. In dropping from 1100psi to 400 psi, the computer system 99 allows the pressure to vent slowly from the drying chamber 40. In addition, the computer system 99 commands the heater 33 disposed on the drying chamber 40 to maintain the temperature of the drying chamber 40 at 31° C. or above.

At S1610 to S1620, when the drying chamber pressure reaches 400 psi however, the software instructions command the computer system 99 to shut off the heaters and vent the remaining pressurized gas from inside the drying chamber 40 directly out the vent line. The purge valve 63 is opened and the bleed valve 62 is closed. The purge valve 63 will remain open until another run is commenced or the critical point drying apparatus 1 is powered down.

For the three valve embodiments illustrated in FIGS. 9A and 10A, at S1610 to S 1620, when the drying chamber pressure reaches 400 psi however, the software instructions command the computer system 99 to shut off the heaters and vent the remaining pressurized gas from inside the drying chamber 40 directly out the vent line. The purge valve 63 will remain open until another run is commenced or the critical point drying apparatus 1 is powered down.

Referring to FIG. 16, a tabular summary of the operational modes of the critical point drying apparatus 1 are shown. For the three valve embodiments depicted in FIGS. 9A and 10A, the purge valve 63 also performs the functions of the bleed valve as well.

In another aspect of the present invention, the predetermined operations of the software instructions comprise instructions for conducting diagnostic testing of several sensors used to control the critical point drying sequence. The software instructions test the high pressure sensor 67 (or critical point pressure sensor), the low pressure sensor 68, the heat sensor 31 and cool sensor 32. The computer system 99 executing the software instructions indicates on the display if each of the above-identified sensors is operational. Preferably, the computer system 99 lights an operation indication LED that indicates to the operator that the sensor is working properly.

The predetermined operations of the software instructions also comprise diagnostic instructions that support the testing of switches, their corresponding operation indication LED switches and microprocessor interrupt service routine. For example, to test the purge LED switch 18, pressing the purge LED switch 18 while the critical point drying apparatus 1 is powered up will cause the purge LED switch 18 to light if the computer system 99 is executing the software correctly. In another example, pressing the heat LED switch 19 when powering up the apparatus causes the operation indication LEDs to individually light in sequence, thereby indicating that the microprocessor clock is operating correctly. Preferably, the operation indication LEDs light sequentially in fifteen-second intervals.

The predetermined operations of the software instructions also comprise calibration instructions for the cool sensor 32. The computer system 99 will cool the drying chamber 40 independently of the cool sensor 32. The fill LED switch 17 will indicate the status of the cool sensor 32 and will allow the operator to determine if the cool sensor 32 is operating correctly or that it needs adjustment.

The predetermined operations of the software instructions also comprise instructions to ensure that the buildup of static electricity does not affect the operation indication LED switches. The computer system 99 constantly checks the status of the operation indication LED switches to ensure that they are operating properly. If an operation indication LED has prematurely switched off, the computer system 99 determines at what point of the critical point drying sequence the critical point drying apparatus 1 is in, and then switches on the appropriate operation indication LED.

Another aspect of the present invention will now be discussed. The present invention may be embodied on a computer program product for enabling a computer system to perform critical point drying techniques when coupled to a critical point drying apparatus. The software instructions that enable the computer system to perform predetermined operations as required by the present invention are borne on a computer readable medium. The predetermined operations borne on the computer program product comprise software instructions for cooling the drying chamber to a first chamber temperature. Preferably, the first chamber temperature is between 5 and —10° C.

The predetermined operations borne on the computer program product further comprise software instructions for filling the drying chamber 40 with a transitional fluid having a critical point temperature and critical point pressure while maintaining the drying chamber 40 at the first chamber temperature such that the transitional fluid completely displaces the intermediary fluid within a first time period. As noted above, the first chamber temperature is preferably between 5 and —10° C. The predetermined operations borne on the computer program product maintains the drying chamber 40 at the first chamber temperature while the intermediary fluid is exhausted from the interior of the drying chamber 40. When the intermediary fluid is purged, the predetermined operations borne on the computer program product ensure that the drying chamber is completely filled with transitional fluid to ensure a successful drying cycle. This is done by going through a quick fill cycle.

The predetermined operations borne on the computer program product further comprise software instructions for activating at least one heater to raise the transitional fluid to its critical point pressure and critical point temperature, thereby reaching a critical point equilibrium. Preferably, the predetermined operations borne on the computer program product command a heater 32 on the drying chamber 40 to heat the transitional fluid to at least 31° C. or above. The predetermined operations borne on the computer program product also notify the operator if the critical point equilibrium was successfully reached.

The predetermined operations borne on the computer program product further comprise software instructions for maintaining the transitional fluid at the critical point equilibrium for a second time period. The predetermined operations borne on the computer program product notify the operator that the transitional fluid in the drying chamber is at its critical point equilibrium.

The predetermined operations borne on the computer program product further comprise software instructions for bleeding the transitional fluid from the drying chamber 40 while maintaining the drying chamber 40 at the second chamber temperature. Preferably, the predetermined operations borne on the computer program product command the at least one heater 32 to maintain a drying chamber temperature of at least 31° C. while the transitional fluid is bled from the drying chamber 40.

Another aspect of the present invention will now be discussed. The present invention may be embodied on an article of manufacture, which comprises a computer readable medium having stored therein a computer program to control a drying chamber during a critical point drying process. The article of manufacture comprises a computer program product that bears a first computer code segment which, when executed on a computer, cools the drying chamber 40 to a first chamber temperature. Preferably, the first chamber temperature is between 5 and –100° C.

The article of manufacture further comprises a second computer code segment which, when executed on a computer, fills the drying chamber 40 with a transitional fluid having a critical point temperature and critical point pressure while maintaining the drying chamber 40 at the first chamber temperature such that the transitional fluid completely displaces the intermediary fluid within a first time period. As noted above, the first chamber temperature is preferably between 5 and –10° C. The second computer code segment, when executed on a computer, maintains the drying chamber 40 at the first chamber temperature while the intermediary fluid is exhausted from the interior of the drying chamber. When the intermediary fluid is purged, the second computer code segment, when executed on a computer, ensures that the drying chamber 40 is completely filled with transitional fluid to ensure a successful drying cycle.

The article of manufacture also comprises a third computer code segment which, when executed on a computer, activates at least one heater to raise the transitional fluid to its critical point pressure and critical point temperature, thereby reaching a critical point equilibrium. Preferably, the third computer code segment commands a heater 32 on the drying chamber 40 to heat the drying chamber 40 to at least 31° C. or above. The third computer code segment, when executed on a computer, also notifies the operator if the critical point equilibrium was successfully reached.

The article of manufacture further comprises a fourth computer code segment which, when executed on a computer, maintains transitional fluid at the critical point equilibrium for a second time period. The fourth computer code segment, when executed on a computer, notifies the operator that the transitional fluid in the drying chamber is at its critical point equilibrium.

Finally, the article of manufacture further comprises a fifth computer code segment which, when executed on a computer, bleeds the transitional fluid from the drying chamber 40 while maintaining the drying chamber 40 at the second chamber temperature. Preferably, the fifth computer code segment, when executed on a computer, commands the at least one heater 32 to maintain a drying chamber temperature of at least 31° C. while the transitional fluid is bled from the drying chamber 40.

The foregoing description of the preferred embodiments of the present invention has been presented for purposes of illustration and description. It is not intended to be exhaustive or to limit the present invention to the precise form disclosed, and modifications and variations are possible in light of the above teachings or may be acquired from practice of the present invention. The embodiments were chosen and described in order to explain the principles of the present invention and its practical application to enable one skilled in the art to utilize the present invention in various embodiments and with various modifications as are suited to the particular use contemplated.

Thus, while only certain embodiments of the present invention have been specifically described herein, it will be apparent that numerous modifications may be made thereto without departing from the spirit and scope of the resent invention. Further, acronyms are used merely to enhance the readability of the specification and claims. It should be noted that these acronyms are not intended to lessen the generality of the terms used and they should not be construed to restrict the scope of the claims to the embodiments described therein.

What is claimed is:

1. A critical point drying apparatus for drying specimens, comprising:
   a drying chamber having concave end portions and at least one heater;
   a first valve assembly that supplies a cooling fluid to the drying chamber;
   a second valve assembly that supplies a transitional fluid having a critical point temperature and critical point pressure to the drying chamber;
   a third valve assembly that allows an intermediary fluid to be purged from the drying chamber;
   a fourth valve assembly that bleeds the transitional fluid from the drying chamber; and
   a computer system that operates the first, second, third and fourth valve assemblies and that activates the at least one heater to heat the transitional fluid above the critical point temperature and to pressurize the transitional fluid above the critical point pressure.

2. The critical point drying apparatus as claimed in claim 1, wherein the third and fourth valve assemblies comprise heaters.

3. The critical point drying apparatus as claimed in claim 2, wherein the third and fourth valve assemblies further comprise check valves to prevent the backflow of intermediary fluid into the drying chamber.

4. The critical point drying apparatus as claimed in claim 1, further comprising a heated pressure relief valve.

5. The critical point drying apparatus as claimed in claim 1, wherein the computer system comprises a plurality of relays to control the first, second, third and fourth valve assemblies.

6. The critical point drying apparatus as claimed in claim 1, wherein the drying chamber is adiabatically cooled.

7. The critical point drying apparatus as claimed in claim 1, wherein the drying chamber has at least one inlet port for the introduction of the transitional fluid into the interior of the drying chamber.

8. The critical point drying apparatus as claimed in claim 7, wherein the at least one inlet port is angled with respect to an inner surface of the drying chamber.

9. The critical point drying apparatus as claimed in claim 1, wherein the drying chamber further comprises mounting posts, wherein the mounting posts are pinned to a sidewall of the drying chamber.

10. The critical point drying apparatus as claimed in claim 1, further comprising a condenser collector that collects intermediary fluid after exiting the third valve assembly.

11. The critical point drying apparatus as claimed in claim 10, wherein the condenser collector comprises a reservoir for heating frozen intermediary fluid.

12. The critical point drying apparatus as claimed in claim 1, wherein the critical point drying apparatus receives cooling fluid from a closed loop refrigeration system.

13. The critical point drying apparatus as claimed in claim 1, wherein the drying chamber further comprises a viewing port.

14. The critical point dryer apparatus as claimed in claim 1, wherein the drying chamber further comprises at least one wafer holder and at least one spacer ring.

15. The critical point dryer apparatus as claimed in claim 14, wherein the drying chamber further comprises at least one chamber insert.

16. A critical point dryer apparatus, comprising:
   a drying chamber having concave end portions and at least one heater; and
   a computer system adapted to control the drying chamber during a critical point drying process, the computer system comprising:
      a processor;
      a memory comprising software instructions adapted to enable the computer system to:
         cool the drying chamber to a first chamber temperature;
         fill the drying chamber with a transitional fluid having a critical point temperature and critical point pressure while maintaining the drying chamber at the first chamber temperature such that the transitional fluid completely displaces an intermediary fluid within a first time period;
         activate at least one heater to raise the transitional fluid to its critical point pressure and critical point temperature, thereby reaching a critical point equilibrium;

maintain the transitional fluid at the critical point equilibrium for a second time period; and bleed the transitional fluid from the drying chamber while maintaining the drying chamber at a second chamber temperature and allowing the drying chamber pressure to drop.

17. The critical point dryer apparatus according to claim 16, wherein the software instructions that fill the drying chamber with transitional fluid are further adapted to fill the drying chamber completely with transitional fluid, by means of a post purge fill cycle.

18. The critical point dryer apparatus according to claim 16, wherein the software instructions that activate at least one heater are further adapted to command the computer system to heat the drying chamber to at least 31° C.

19. The critical point dryer apparatus according to claim 16, wherein the software instructions that activate the at least one heater are further adapted to command the computer system to pressurize the drying chamber pressure to at least 1175 pounds per square inch.

20. The critical point dryer apparatus according to claim 16, wherein the software instructions are further adapted to enable the computer system to perform diagnostic testing on the critical point dryer apparatus.

21. The critical point dryer apparatus according to claim 20, wherein the software instructions are further adapted to enable the computer system to perform diagnostic testing of a sensor mounted on the drying chamber.

22. The critical point dryer apparatus according to claim 16, wherein the software instructions are further adapted to enable the computer system to signal to an operator that the temperature and the pressure of the transitional fluid are above the critical point equilibrium.

23. The critical point dryer apparatus according to claim 22, wherein the software instructions are further adapted to enable the computer system to signal to the operator that the transitional fluid has not reached critical point equilibrium.

24. The critical point dryer apparatus according to claim 16, wherein the software instructions that bleed the transitional fluid from the drying chamber are further adapted to command the computer system to shut off the at least one heater when the drying chamber pressure drops between 600 and 100 pounds per square inch.

25. The critical point dryer apparatus according to claim 24, wherein the software instructions that bleed the transitional fluid from the drying chamber are further adapted to command the computer system to vent the transitional fluid when the drying chamber pressure drops below 400 pounds per square inch.

26. A critical point drying apparatus for drying specimens, comprising:

a drying chamber having at least one heater and further comprising at least one wafer holder;

a first valve assembly that supplies a cooling fluid to the drying chamber;

a second valve assembly that supplies a transitional fluid having a critical point temperature and critical point pressure to the drying chamber;

a third valve assembly that allows an intermediary fluid to be purged from the drying chamber, and that bleeds the transitional fluid from the drying chamber; and a computer system that operates the first, second and third valve assemblies and that activates the at least one heater to heat the transitional fluid above the critical point temperature and to pressurize the transitional fluid above the critical point pressure.

27. The critical point dryer apparatus as claimed in claim 26, wherein the drying chamber further comprises at least one chamber insert.

28. A critical point drying apparatus for drying specimens, comprising:

a drying chamber having concave end portions and at least one heater;

a first valve assembly that supplies a cooling fluid to the drying chamber;

a second valve assembly that supplies a transitional fluid having a critical point temperature and critical point pressure to the drying chamber;

a third valve assembly that allows an intermediary fluid to be purged from the drying chamber, and that bleeds the transitional fluid from the drying chamber; and a computer system that operates the first, second and third valve assemblies and that activates the at least one heater to heat the transitional fluid above the critical point temperature and to pressurize the transitional fluid above the critical point pressure.

29. The critical point dryer apparatus as claimed in claim 28, wherein the drying chamber further comprises at least one wafer holder.

30. The critical point dryer apparatus as claimed in claim 28, wherein the drying chamber further comprises at least one chamber insert.

\* \* \* \* \*